US006511828B1

(12) United States Patent
Thompson et al.

(10) Patent No.: US 6,511,828 B1
(45) Date of Patent: Jan. 28, 2003

(54) HUMAN AND DROSOPHILA INHIBITORS OF APOPTOSIS PROTEINS (IAPS)

(75) Inventors: Craig B. Thompson, Chicago, IL (US); Colin S. Duckett, Chicago, IL (US)

(73) Assignee: Arch Development Corporation, Chicago, IL (US)

( * ) Notice: Subject to any disclaimer, the term of this patent is extended or adjusted under 35 U.S.C. 154(b) by 0 days.

(21) Appl. No.: 08/657,759

(22) Filed: May 31, 1996

(51) Int. Cl.[7] ........................ C12N 15/00; C12N 15/09; C12N 1/20; C07H 21/04

(52) U.S. Cl. .................. 435/69.2; 435/69.1; 435/320.1; 435/325; 435/252.3; 536/23.1; 536/23.5

(58) Field of Search ............................... 536/23.5, 23.1; 435/69.2, 70.2, 320.1, 325, 252.3, 69.1

(56) References Cited

U.S. PATENT DOCUMENTS

| | | | |
|---|---|---|---|
| 5,919,912 A | | 7/1999 | Korneluk et al. |
| 6,020,127 A | | 2/2000 | MacKenzie et al. |
| 6,107,041 A | | 8/2000 | Korneluk et al. |
| 6,107,088 A | | 8/2000 | Korneluk et al. |
| 6,133,437 A | | 10/2000 | Korneluk et al. |
| 6,156,535 A | | 12/2000 | Korneluk et al. |
| 6,159,709 A | | 12/2000 | Korneluk et al. |
| 6,159,948 A | | 12/2000 | Robertson et al. |
| 6,171,821 B1 | | 1/2001 | Korneluk et al. |
| 6,187,557 B1 | * | 2/2001 | Rothe et al. |
| 6,300,492 B1 | | 10/2001 | Korneluk et al. |
| 6,331,412 B1 | | 12/2001 | Korneluk et al. |

OTHER PUBLICATIONS

Hay et al., Cell vol. 83: 1253–1262, Dec. 1995.*

Liston et al., Nature, vol. 379:349–353, Jan. 1996.*

MPsearch sequence alignment, Jan. 1997.*

Campbell, Monoclonal antibody technology, pp. 1–32, Jan. 1985.*

Hay et al., "Drosophila Homologs of Baculovirus Inhibitor of Apoptosis Proteins Function to Block Cell Death" *Cell, 83*:1253–1262, 1995.

* cited by examiner

*Primary Examiner*—David Guzo
*Assistant Examiner*—Gerald G. Leffers, Jr.
(74) *Attorney, Agent, or Firm*—Fulbright & Jaworski

(57) ABSTRACT

A new family of proteins having structural similarity to the baculovirus inhibitor of apoptosis protein (iap) are described. These ilp's (iap-like proteins) are distinguished by the presence of a RING finger domain and three baculovirus iap-like repeat motifs. Exemplified are sequences from Drosophila and human. Methods for the use of these proteins, and nucleic acids coding therefor, are provided. These methods include both the inhibition and stimulation of apoptosis in target cells.

6 Claims, 7 Drawing Sheets

```
  1 MTELGMELES VRLATFGEWP LNAPVSAEDL VANGFFATGN WLEAECHFCH
 51 VRIDRWEYGD QVAAGHRRSS PICSMVLAPN HCGNVPRSQE SDNEGNSVVD
101 SPESCSCPDL LLEANRLVTF KDWPNPNITP QALAKAGFYY LNRLDHVKCV
151 WCNGVIAKWE KNDNAFEEHK RFFPQCPRVQ MGPLIEFATG KNLDELGIQP
201 TTLPLRPKYA CVDARLRTFT DWPISNIQPA SALAQAGLYY QKIGDQVRCF
251 HCNIGLRSWQ KEDEPWFEHA KWSPKCQFVL LAKGPSYVSE VLATTAANAS
301 SPPATAPAPT LQADVLMDEA PAKEALALGI DGGVVRNAIQ RKLLSSGCAF
351 STLDELLHDI FDDAGAGADW RCASREPSAP FIEPCQATTS KAASVPIPVA
401 DSIPAKPQAA EAVANISKIT DEIQKMSVAT PNGNLSLEEE NRQLKDARLC
451 KVCLDEEVGV VFLPCGHLAT CNQCAPSVAN CPMCRADIKG FVRTFLS*
```

FIG.2B

```
  1 MTFNSFEGSK TCVPADINKE EEFVEEFNRL KTFANFPSGS PVSASTLARA
 51 GFLYTGEGDT VRCFSCHAAV DRWQYGDSAV GRHRKVSPNC RFINGFYLEN
101 SATQSTNSGI QNGQYKVENY LGSRDHFALD RPSETHADYL LRTGQVVDIS
151 DTIYPRNPAM YSEEARLKSF QNWPDYAHLT PRELASAGLY YTGIGDQVQC
201 FCCGGKLKNW EPCDRAWSEH RRHFPNCFFV LGRNLNIRSE SDAVSSDRNF
251 PNSTNLPRNP SMADYEARIF TFGTWIYSVN KEQLARAGFY ALGEGDKVKC
301 FHCGGGLTDW KPSEDPWEQH AKWYPGCKYL LEQKGQEYIN NIHLTHSLEE
351 CLVRTTEKTP SLTRRIDDTI FQNPMVQEAI RMGFSFKDIK KIMEEKIQIS
401 GSNYKSLEVL VADLVNAQKD SMPDESSQTS LQKEISTEEQ LRRLQEEKLC
451 KICMDRNIAI VFVPCGHLVT CKQCAEAVDK CPMCYTVITF KQKIFMS*
```

FIG.2C

```
KNKAARLGTYTNWP--VQFLEPSRMAASGFYYLGRGDEVRCAFCKVEITNWVRGDDPETDHKRWAPQCPFVRNNA   OpMNPV BIR 1
ATEAARLRTFAEWP-RGLKQRPEELAEAGFFYTGQGDKTRCFCCDGGLKDWEPDDAPWQQHARWYDRCEYVLLVK   OpMNPV BIR 2

ELESVRLATFGEWPL-NAPVSAEDLVANGFFATGNWLEAECHFCHVRIDRWEYGDQVAAGHRRSSPICSMVLAPN   Dros ILP BIR a
LLEANRLVTFKDWP--NPNITPQALAKAGFYYLNRLDHVKCVWCNGVIAKWEKNDNAFEEHKRFFPQCPRVQMGP   Dros ILP BIR b
ACVDARLRTFTDWP-ISNIQPASALAQAGLYYQKIGDQVRCFHCNIGLRSWQKEDEPWFEHAKWSPKCQFVLLAK   Dros ILP BIR c

VEEFNRLKTFANFPS-GSPVSASTLARAGFLYTGEGDTVRCFSCHAAVDRWQYGDSAVGRHRKVSPNCRFINGFY   Hum ILP BIR a
YSEEARLKSFQNWPDYAH-LTPRELASAGLYYTGIGDQVQCFCCGGKLKNWEPCDRAWSEHRRHFPNCFFVLGRN   Hum ILP BIR b
ADYEARIFTFGTWI-YSVNK--EQLARAGFYALGEGDKVKCFHCGGGLTDWKPSEDPWEQHAKWYPGCKYLLEQK   Hum ILP BIR c

RSEAKRLKTFVTYEPYSSWI-PQEMAAAGFYFTGVKSGIQCFCCSLILFGAGLTRLPIEDHKRFHPDCGFLLNKD   Hum NAIP BIR a
QEEEARLASFRNWPFYVQGISPCVLSEAGFVFTGKQDTVQCFSCGGCLGNWEEGDDPWKEHAKWFPKCEFLRSKK   Hum NAIP BIR b
AYEELRLDSFKDWPRESA-VGVAALAKAGLFYTGIKDIVQCFSCGGCLEKWQEGDDPLDDHTRCFPNCPFLQNMK   Hum NAIP BIR c

----ARL-TF--WP----------LA-AGFYYTG-GD-V-CF-C-G-L--W---D-P---H-R--P-C-FVL---   Consensus
---------------------------------------C--C---------------H------C-------   Cys/His
```

FIG.3A

```
218   DRLCKICLGAEKTVCFV.PCGHVVACGKC..A.AGVT..TCPVCRGQ   OpMNPV IAP
447   ARLCKVCLDEEVGVVFL.PCGHLATCNQC..A.PAVA..NCPMCRAD   Dros ILP
447   EKLCKICMDRNIAIVFV.PCGHLVTCKQC..A.EAVD..KCPMCYTV   Hum ILP

 31   KYLCSACKNILRRPFQA.QCGHRY.CSFCLTSILSSGPQNCAACVYE   TRAF2
 50   KYKCEKCHLVLCSPKQT.ECGHRF.CESCMAALLSSSSPKCTACQ.E   CRAF1
378   FQLCKICAENDKDVKIE.PCGHLM.CTSCLTSWQESEGQGCPFCRCE   c-Cbl
 16   ELMCPICLDMLKNTMTTKECLHRF.CSDCIVTALRSGNKECPTCRKK   RING1
 54   FLRCQQCQAEAKCPKLL.PCLHTL.CSGCLE.A.SGM.Q.CPICQAP   c-Pml

                 X11-12                X6-11
         C..C............C.H...C..C...........C..C...   Consensus
```

FIG.3B

HUMAN AND DROSOPHILA INHIBITORS OF APOPTOSIS PROTEINS (IAPS)

The government may own certain rights in this application by virtue of federal funding under grant no. PO1 DK49799 from the National Institutes of Health.

BACKGROUND OF THE INVENTION

I. Field of the Invention

The present invention relates to the fields of molecular and cell biology generally, and more specifically, it addresses mechanisms for growth control in eurkaryotic cells. In particular, there are provided genes that inhibit normal cell death and methods for use thereof.

II. Related Art

The control of host cell translation, and often the control of replication, are integral parts of the life cycle of a virus. However, recent evidence suggests that most eurkaryotic cells respond to viral disruption of normal cellular physiology by undergoing programmed cell death (apoptosis) (White, 1993). To counteract this, many viruses have evolved mechanisms to block host cell death (Clem and Miller, 1994a; White and Gooding, 1994). In several cases, viral genomes have been found to contain genes whose products interact with proteins that play a central role in regulating cell survival.

For example, the product of the crmA gene isolated from cowpox virus can inhibit apoptosis through its ability to inhibit members of the interleukin-1β-converting enzyme (ICE) protease family (Miura et al., 1993; Yuan et al., 1993; Gagliardini et al., 1994; Komiyama et al., 1994; Kumar et al., 1994; Wang et al., 1994; Fernandes-Alnemri et al., 1995; Los et al., 1995; Tewari et al., 1995). The E1B 19 kD protein of adenovirus also can protect cells from death induced by a wide variety of stimuli (Debbas and White, 1993; Sabbatini et al., 1995). The ability of E1B 19 kD to protect cells from apoptosis correlates with its ability to bind to members of the bcl-2 family that promote cell death (Chiou et al., 1994; Farrow et al., 1995).

Insect baculoviruses contain at least two independent genes that promote the survival of the infected host cell-p35 (Friesen and Miller, 1987; Clem et al., 1991; Hershberger et al., 1992; Clem and Miller, 1993; Kamita et al., 1993; Hershberger et al., 1994) and iap (Crook et al., 1993; Birnbaum et al., 1994). Recombinant baculoviruses lacking both genes induce accelerated host cell death leading to severely impaired virus production (Clem and Miller, 1994b). Although p35 and iap have no sequence similarity, they are functionally equivalent in the context of the virus. When provided in trans either gene can protect host cells from death induced by a baculovirus lacking both genes (Clem and Miller, 1994b). This suggests that p35 and iap exert their effects at key points in the cellular apoptotic pathway.

Consistent with this view is the discovery that p35 can confer protection from cell death in mammalian cells (Rabizadeh et al., 1993; Beidler et al., 1995), an observation which reflects the high degree of evolutionary conservation of the apoptotic cell death pathway (Vaux et al., 1994; White et al., 1994). Recently, p35 has been shown to act by blocking the activity of members of the ICE family of cysteine proteases (Bump et al., 1995; Xue and Horvitz, 1995). Whether iap also blocks an evolutionarily conserved step in apoptosis has not been determined. The iap genes isolated from different baculoviruses all display similar structural features.

The utility of proteins that are capable of inhibiting apoptosis are manifold. First, such proteins, or their corresponding genes, may be used to immortalize cell lines that otherwise would perish during culture. This makes possible not only the study of these cells, but also presents the option of growing these cells in large numbers in order to isolate protein species therefrom. Second, the identification of iap's and their function permits the possible intervention, in a clinical setting, when these proteins are interfering with normal programmed cell death, or apoptosis. This may be accomplished by providing an ilp inhibitor or an antisense nucleic acid that interferes with the expression of an ilp protein. Thus, the identification of novel proteins having these activities and uses provide important new tools for those working in this arena.

SUMMARY OF THE INVENTION

It is, therefore, an object of the present invention to provide new ilp proteins and gene coding therefor. It also is an object of the present invention to provide methods of using these new proteins, for example, in the immortalization of cells for culture, for inhibiting the activation of cysteine proteases and to sustain host cell survival following viral infection. It also is contemplated that, through the use of other technologies such as antisense expression and antibody treatment, one can treat certain cancers by inhibiting the effects of these new ilp proteins.

Therefore, there is provided an isolated and purified ilp comprising at least three BIR domains and a ring finger domain, wherein the ilp has at least one of the activities of (i) inhibition of apoptosis, (ii) inhibition of cysteine protease activation and (iii) inhibition of virus-induced cell death. In a preferred embodiment, the ilp will have all three of these activities. In another embodiment, the ring finger domain is carboxy-terminal to the BIR domains, and in yet another embodiment, an amphipathic domain separates the BIR domains and the ring finger domain. The amphipathic domain preferably is between about 120 and 170 amino acids. The ilp may be a human protein, as in FIG. 2C (SEQ ID NO:2). The ilp may be a Drosophila protein, as in FIG. 2B (SEQ ID NO:1).

In another embodiment, there is provided an isolated and purified polynucleotide encoding an ilp, the ilp comprising at least three BIR domains and a ring finger domain, wherein the ilp has at least one of the activities of (i) inhibition of apoptosis, (ii) inhibition of cysteine protease activation and (iii) inhibition of virus-induced cell death. The polynucleotide may be of human or Drosophila origin.

In yet another embodiment, a recombinant host cell comprising a polynucleotide encoding an ilp, said ilp comprising at least three BIR domains and a ring finger domain, wherein said ilp has at least one of the activities of (i) inhibition of apoptosis, (ii) inhibition of cysteine protease activation and (iii) inhibition of virus-induced cell death.

In still yet another embodiment, there is provided an antibody that is immunologically reactive with an ilp comprising at least three BIR domains and a ring finger domain, wherein the ilp has at least one of the activities of (i) inhibition of apoptosis, (ii) inhibition of cysteine protease activation and (iii) inhibition of virus-induced cell death.

In still yet another embodiment, there is provided a method for producing an ilp comprising at least three BIR domains and a ring finger domain, wherein the ilp has at least one of the activities of (i) inhibition of apoptosis, (ii) inhibition of cysteine protease activation and (iii) inhibition of virus-induced cell death, comprising the steps of (a)

providing a recombinant host cell comprising a polynucleotide encoding said ilp and (b) culturing said recombinant host cell. In a further step, there is provided a step of isolating the ilp.

In still yet another embodiment, there is provided a method for inhibiting apoptosis comprising the step of providing to a cell an ilp comprising at least three BIR domains and a ring finger domain, wherein the ilp has the activity of inhibition of apoptosis. The method preferably comprises contacting by transforming said cell with said polynucleotide. Transforming may be accomplished by viral-mediated gene transfer, receptor-mediated gene transfer, liposome-mediated gene transfer, calcium phosphate-mediated gene transfer or direct gene injection.

In still yet another embodiment, there is provided a method for inducing apoptosis comprising blocking the expression in a cell of an ilp comprising at least three BIR domains and a ring finger domain, wherein the ilp has the activity of inhibition of apoptosis. The method preferably comprises providing to a cell an antisense polynucleotide corresponding to a portion of the ilp. The providing preferably comprises transforming the cell, and the transforming may be by viral-mediated gene transfer, receptor-mediated gene transfer, liposome-mediated gene transfer, calcium phosphate-mediated gene transfer and direct gene injection.

In still yet another embodiment, there is provided a method for inhibiting apoptosis comprising increasing the level in a cell of an ilp comprising at least three BIR domains and a ring finger domain, wherein the ilp has the activity of inhibition of apoptosis. In one method, the increasing comprises providing to the cell an ilp. Alternatively, the increasing comprises stimulating the expression of an endogenous ilp. In this embodiment, the cell may be transformed with a polynucleotide encoding the ilp. The transforming may be by viral-mediated gene transfer, receptor-mediated gene transfer, liposome-mediated gene transfer, calcium phosphate-mediated gene transfer and direct gene injection.

In still yet another embodiment, there is provided a method for inhibiting cysteine protease activation comprising the step of providing to a cell an ilp comprising at least three BIR domains and a ring finger domain, wherein the ilp has the activity of inhibition of cysteine protease activation. Alternatively, the method may comprise the step of providing to a cell a polynucleotide encoding an ilp, the ilp comprising at least three BIR domains and ring finger domain, wherein the ilp has the activity of inhibition of cysteine protease activation.

In still yet another embodiment, there is provided a method for inhibiting virus-induced cell death comprising the step of providing to a cell an ilp comprising at least three BIR domains and a ring finger domain, wherein the ilp has the activity of inhibition of virus-induced cell death. Alternatively, the method may comprise the step of providing to a cell a polynucleotide encoding an ilp, the ilp comprising at least three BIR domains and ring finger domain, wherein the ilp has the activity of inhibition of virus-induced cell death.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Baby hamster kidneys (BHK) cells were infected with recombinant Sindbis viruses containing Op-iap; Op-iap containing a premature stop codon (Op-iap/stop); bcl-$x_L$; bcl-$x_L$ gene containing a premature stop (bcl-$x_L$/stop); or with media alone (mock). Cell viability was assayed 48 hrs after viral infection, and viability was measured by trypan blue exclusion. Data expressed is mean±standard error of 3 or more independent experiments. (FIG. 1B) The viability of N18 mouse neuroblastoma cells infected and assayed as above. (cat) refers to infection with a Sindbis virus containing a chloramphenicol acetyltransferase gene.

FIGS. 2A, 2B and 2C: Predicted amino acid sequences of the iap-related genes, dilp and hilp. (FIG. 2A) A schematic representation of the organization of Op-iap, dilp, and hilp is described and the localization of the BIR and RING finger domains is shown. (FIGS. 2B and 2C) Sequences of dilp (SEQ ID NO:1) and hilp (SEQ ID NO:2), respectively.

FIGS. 3A and 3B: Viral iap and cellular ilp genes share two conserved domains: BIR repeats and RING fingers. (FIG. 3A) Alignment of the BIR repeats in the iap protein of *Orgyia pseudotsugata* nuclear polyhedrosis virus (OpMPNPV), Drosophila ilp, human ilp, and human NAIP genes (SEQ ID NO:3–25). Amino acids that are identical in more than half of these BIR domains are shaded. An amino acid consensus, as well as location of conserved cysteines and histidines, are indicated below the alignment. (FIG. 3B) Alignment of the RING ringer domains between viral iap, Drosophila ILP, and human ilp, as well as several well characterized human RING finger domains (SEQ ID NO:26–52). The characteristic cysteine and histidine spacing of a RING finger domain is shown as a consensus sequence.

DETAILED DESCRIPTION OF THE INVENTION

Figure 1A:
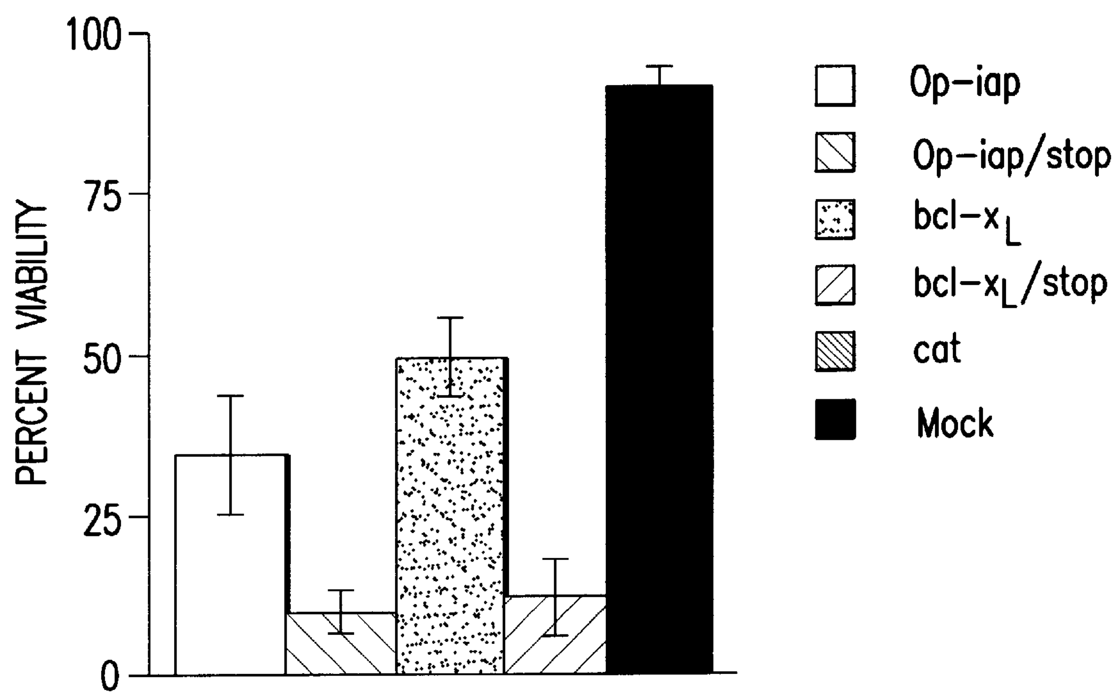
FIGS. 1A and 1B: Baculovirus iap can protect cells from apoptosis induced in response to Sindbis virus infection.

To obtain further insight into the role of baculovirus iap's in regulating apoptotic cell death, the properties of iap's were examined in the context of a viral infection of mammalian cells. It was determined that baculovirus iap is able to prevent cell death induced by infection of mammalian cell lines with Sindbis virus, suggesting that this protein might prevent apoptosis by mimicking the actions of an evolutionarily conserved regulator of the cell death pathway. It also was observed that iap's were able to prevent the activation of pro-ICE proteases. This observation has significant ramifications, for example, in the ability to inhibit protease activation of certain biologically active proteins such as IL-1.

Cellular homologs to iap now have been demonstrated in two other organisms. The present inventors have identified human and Drosophila iap-like genes, dilp and hilp, that appear to be widely expressed in their species of origin. Like iap, human ilp was found to protect cells from apoptosis induced both by virus infection and ICE expression. Interestingly, these polypeptides are structurally distinct from the iap-like protein reported by Roy et al., 1995, as their so-called "neuronal apoptosis inhibitory protein" has no ring finger domain. These findings suggest that the ilp proteins described herein represent a new family of cellular factors which are involved in modulating cell survival. The following provides a more detailed explanation of the invention in its various embodiments.

I. ILP's

The present invention involves the identification of a new family of proteins termed here ilp's, or iap-like proteins. The proteins are defined both in terms of structural and functional characteristics. From a structural standpoint, the family is defined as having a RING finger domain and at least three baculovirus iap-like repeat (BIR) sequences. The first of these, the RING finger, is a zinc-binding domain known (Lovering et al., 1993), which also has been identified in a number of cellular proteins including the products of the proto-oncogenes c-cbl (Blake et al., 1991) and c-pml (de The et al., 1991), as well as the recently described family of signal transducing molecules TRAF2 (Rothe et al., 1994; Song and Donner, 1995) and CRAF1/CD40bp (Cheng et al., 1995; Hu et al., 1994; Sato et al., 1995). While RING domains have been found in several DNA-binding proteins, they have not been shown to bind DNA, and probably act to mediate protein-protein interactions (Borden et al., 1995). The second highly conserved feature of baculovirus iap proteins, the BIR, is an amino terminal repeat of an approximately 65 amino acid sequence. Both the BIR repeats and RING domains have been shown to be essential in preventing cell death in insect cells (Clem and Miller, 1994b).

In preferred embodiments, the present invention encompasses ilp's from Drosophila or human. In more preferred embodiments, the proteins have the amino acid sequence of FIG. 2B (SEQ ID NO:1) or 2C, (SEQ ID NO:2), respectively.

The ilp's of the present invention also are characterized by the functional feature of being able to inhibit apoptosis. Apoptosis, or programmed cell death, is characterized by certain cellular events, including nuclear condensation, DNA fragmentation, cytoplasmic membrane blebbing and, ultimately, irreversible cell death. Apoptosis is an energy-dependent event.

Another functional feature of ilp's is their ability to inhibit the activation of cysteine proteases. This ability is significant in that members of this family of protease are responsible for activating a variety of biologically active polypeptides, for example, IL-1β. The ability to block the activation of pro-ICE proteases, therefore, can prevent activation of IL-1β. This, in turn, can limit inflammation caused by IL-1β.

A third functional attribute of ilp's is their ability to protect cells from virus-induced cell death. This observation permits yet another utilization of ilp's according to the present invention. When cells are infected with viruses for the purpose of virus production (for example, in generating vectors), the premature death of the cell can limit the titer of virus produced. If the cell can be sustained longer, the titer of the virus stocks produced should increase.

The ilp's of the present invention may advantageously be cleaved into fragments for use in further structural or functional analysis, or in the generation of reagents such as ilp-related antigens and ilp-specific antibodies. This can be accomplished by treating purified or unpurified ilp's with a peptidase such as endoproteinase glu-C (Boehringer, Indianapolis, Ind.). Treatment with CNBr is another method by which ilp fragments may be produced from natural ilp's. Recombinant techniques also can be used to produce specific fragments of ilp's.

Changes may made in the sequence of ilp's, while retaining a molecule having the structure and function of the natural ilp. For example, certain amino acids may be substituted for other amino acids in a protein structure without appreciable loss of interactive capacity with structures such as, for example, antigen-binding regions of antibodies or binding sites on substrate molecules. These changes are termed "conservative" in the sense that they preserve the structural and, presumably, functional qualities of the starting molecule.

Conservative amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as equivalent.

In making such changes, the hydropathic index of amino acids also may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the polypeptide created is intended for use in immunological embodiments, as in the present case. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

Numerous scientific publications have been devoted to the prediction of secondary structure, and to the identification of epitopes, from analyses of amino acid sequences (Chou & Fasman, 1974a,b; 78a,b; 1979). Any of these may be used, if desired, to supplement the teachings of Hopp in U.S. Pat. No. 4,554,101. Moreover, computer programs are currently available to assist with predicting antigenic portions and epitopic core regions of proteins. Examples include those programs based upon the Jameson-Wolf analysis (Jameson & Wolf, 1998; Wolf et al., 1988), the program PepPlot® (Brutlag et al., 1990; Weinberger et al., 1985), and other new programs for protein tertiary structure prediction (Fetrow & Bryant, 1993).

Two designations for amino acids are used interchangeably throughout this application, as is common practice in the art. Alanine=Ala (A); Arginine=Arg (R); Aspartate=Asp (D); Asparagine=Asn (N); Cysteine=Cys (C); Glutamate=Glu (E); Glutamine=Gln (Q); Glycine=Gly (G); Histidine=His (H); Isoleucine=Ile (I); Leucine=Leu (L); Lysine=Lys (K); Methionine=Met (M); Phenylalanine=Phe (F); Proline=Pro (P); Serine=Ser (S); Threonine=Thr (T); Tryptophan=Trp (W); Tyrosine=Tyr (Y); Valine=Val (V).

TABLE I

| Amino Acid | Hydropathic Index |
|---|---|
| Isoleucine | 4.5 |
| Valine | 4.2 |
| Leucine | 3.8 |
| Phenylalanine | 2.8 |
| Cysteine/cystine | 2.5 |
| Methionine | 1.9 |
| Alanine | 1.8 |
| Glycine | −0.4 |
| Threonine | −0.7 |
| Tryptophan | −0.9 |
| Serine | −0.8 |
| Tyrosine | −1.3 |
| Proline | −1.6 |
| Histidine | −3.2 |
| Glutamic Acid | −3.5 |
| Glutamine | −3.5 |
| Aspartic Acid | −3.5 |
| Asparagine | −3.5 |
| Lysine | −3.9 |
| Arginine | −4.5 |

TABLE II

| Amino Acid | Hydrophilic Index |
|---|---|
| arginine | +3.0 |
| lysine | +3.0 |
| aspartate | +3.0 ± 1 |
| glutamate | +3.0 ± 1 |
| serine | +0.3 |
| asparagine | +0.2 |
| glutamine | +0.2 |
| glycine | 0 |
| threonine | −0.4 |
| alanine | −0.5 |
| histidine | −0.5 |
| proline | −0.5 ± 1 |
| cysteine | −1.0 |
| methionine | −1.3 |
| valine | −1.5 |
| leucine | −1.8 |
| isoleucine | −1.8 |
| tyrosine | −2.3 |
| phenylalanine | −2.5 |
| tryptophan | −3.4 |

The present invention also encompasses variants of ilp's that are insertion or deletion variants. Deletion variants lack one or more residues of the native protein. Insertion and replacement variants include sequences in addition to those of ilp's or in lieu of those in ilp's, respectfully, and encompass "fusion" proteins such as those used to permit rapid purification of the protein, immunologically "tagged" proteins and hybrid proteins containing sequences from related proteins.

In addition to the peptidyl compounds described herein, the inventors also contemplate that other sterically similar compounds may be formulated to mimic the key portions of the peptide structure, called peptidomimetics. Mimetics are peptide-containing molecules which mimic elements of protein secondary structure. See, for example, Johnson et al. (1993). The underlying rationale behind the use of peptide mimetics is that the peptide backbone of proteins exists chiefly to orient amino acid side chains in such a way as to facilitate molecular interactions, such as those of antibody and antigen. A peptide mimetic antigen of the present invention would, when administered to a host, elicit an immune response which would lead to recognition of the native parasite antigen.

Successful applications of the peptide mimetic concept have thus far focused on mimetics of β-turns within proteins, which are known to be highly antigenic. Likely β-turn structures within an antigen of the invention can be predicted by computer-based algorithms as discussed above. Once the component amino acids of the turn are determined, mimetics can be constructed to achieve a similar spatial orientation of the essential elements of the amino acid side chains, as discussed in Johnson et al., supra.

II. Use of ILP's as Standards

Another aspect of the present invention concerns the use of the ilp's disclosed herein in the determination of molecular weights of low- to intermediate-sized proteins and polypeptides. It may be used as a marker in the gel separation procedure known as SDS-PAGE. In SDS-PAGE applications, the protein sample is treated with sodium dodecyl sulfate (SDS), a detergent, and then applied to an SDS-containing gel. SDS is an ionic detergent that denatures the proteins in the sample and binds to the uncoiled molecule. The SDS molecules mask the surface charge of the native proteins and create a net negative charge resulting from the $SO_4$ groups on the SDS molecule. All proteins are negatively charged and migrate toward the anode. As all of the surface charges are negative, the speed of migration of the proteins through the gel occurs on the basis of size, with smaller sized molecules traveling faster through the gel as they present less resistance.

As the proteins are separated on the basis of size, the molecular weight of an unknown can be estimated by running standard proteins of known molecular weights on the same gel. Ilp's are particularly contemplated for use as a standard protein for sizing unknown proteins, generally in the 20–30–40 kD range. Commercially-available standards typically have 10 proteins sized between about 6 kD and about 205 kD, but only one standard is in the 30 kD range, that being bovine erythrocyte carbonic anhydrase of 29 kD. Ilp's may be employed as a standard in both conventional SDS-PAGE, as described by Laemmli et al. (1970), and gradient SDS-PAGE. Nucleic acids according to the present invention, discussed below, may also be used as molecular weight standards in gel electrophoresis.

Ilp's also may be used in typical gel filtration protocols, which are also well-known to those of skill in the art. In gel filtration, proteins are applied to a column and their elution position monitored and compared to that of other proteins of known size. The size of the protein determines the degree of inclusion or exclusion. Therefore, a comparison of the elution position allows the size of the unknown protein to be determined. In particular, a regression line of the elution position versus the log of the molecular weight is established for the known and unknown proteins, allowing the molecular weight of the unknown to be calculated.

Here, ilp's will again provide a standard for the calibration of chromatographic columns used in the separation of proteins and polypeptides generally in the 30 kD range. Chromatographic media of the G-50 Sephadex® series, with an approximate fractionation range of 1.5–30 kD, may be used for such separation. However, other media also may be employed, such as the G-75 Sephadex® series, with an approximate fractionation range of 3–70 or 3–80 kD; the G-100 Sephadex® series, with an approximate fractionation range of 4–100 or 4–150 kD; the G-150 Sephadex® series, with an approximate fractionation range of 5–300 or 5–150 kD; or the G-200 Sephadex® series, with an approximate fractionation range of 5–600 or 5–250 kD (SIGMA, St. Louis, Mo.). In addition, PDX, Sephacryl®, Sepharose®, Superose® and Superdex® may also be used as column material (SIGMA).

A further use of the ilp's of the present invention is its use as a standard in protein concentration determinations. As ilp's include certain aromatic amino acids, it has a definite use as a standard reagent in reactions employing the Folin reagent (Lowry et. al., 1951). Ilp's may also be used as a protein concentration standard in assays such as the biuret reaction (Coakley and James, 1978) and the protein concentration assay described by Bradford (1976).

III. Nucleic Acids Encoding ILP's

Also contemplated by the present invention are nucleic acids encoding ilp's. Because of the degeneracy of the genetic code, many other nucleic acids also may encode a given ilp. For example, four different three-base codons encode the amino acids alanine, glycine, proline, threonine and valine, while six different codons encode arginine, leucine and serine. Only methionine and tryptophan are encoded by a single codon. A table of amino acids and the corresponding codons is presented herein for use in such embodiments.

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AU |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

In order to generate any nucleic acid encoding a given ilp, one need only refer to the preceding codon table. Substitution of the natural codon with any codon encoding the same amino acid will result in a distinct nucleic acid that encodes the ilp. As a practical matter, this can be accomplished by site-directed mutagenesis of the ilp sequence or de novo chemical synthesis of one or more nucleic acids.

The preceding observations regarding codon selection, site-directed mutagenesis and chemical synthesis apply with equal force to the discussion of substitutional mutants in the section of peptides. Normally, substitutional mutants are generated by site-directed changes in the nucleic acid of ilp designed to alter one or more codons of the ilp coding sequence.

It also is possible to design specific nucleic acids based on ilp's for uses such as probes and primers. The nucleic acid probes that would be useful in the above-noted hybridization studies may be derived from any portion of the coding region for an ilp. Probes comprise about 8, 9, 10, 11, 12, 13, 14, 15, 16, 17, 18, 19, 20, 25, 30, 35, 40, 45, 50, 60, 70, 80, 90, 100 or more linear nucleotides of the ilp nucleotide sequence. For example, using the nucleotide sequence of Genbank accession numbers U32393 or U32974, the probe sequence is designated by the formula "n to n+y," where n is an integer from 1 the length of U32373 or U32974, and y is the probe length minus 1. Longer probes (100-, 200-, 500- and 1000-mers) that hybridize to ilp genes under low, medium, medium-high and high stringency conditions also are contemplated, including those that comprise the entire nucleotide sequence of U32373 and U32974.

A nucleic acid encoding an ilp, or a fragment or variant thereof, can be inserted into an expression vector by standard subcloning techniques. In one embodiment, an *E. coil* expression vector is used which produces the recombinant antigen as a fusion protein, allowing rapid affinity purification of the protein. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.), and the 6xHis system (Qiagen, Chatsworth, Calif.).

Some of these fusion systems produce recombinant antigen bearing only a small number of additional amino acids, which are unlikely to affect the antigenic ability of the recombinant protein. For example, both the FLAG system and the 6xHis system add only short sequences, both of which are known to be poorly antigenic and which do not adversely affect folding of the protein to its native conformation. Other fusion systems produce proteins where it is desirable to excise the fusion partner from the desired protein. In another embodiment, the fusion partner is linked to the recombinant protein by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

Recombinant bacterial cells, for example *E. coli*, are grown in any of a number of suitable media, for example LB, and the expression of the recombinant antigen induced by adding IPTG to the media or switching incubation to a higher temperature. After culturing the bacteria for a further period of between 2 and 24 hours, the cells are collected by centrifugation and washed to remove residual media. The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars such as sucrose into the buffer and centrifugation at a selective speed.

If the recombinant antigen is expressed in the inclusion bodies, as is the case in many instances, these can be washed in any of several solutions to remove some of the contaminating host proteins, then solubilized in solutions containing high concentrations of urea (e.g. 8M) or chaotropic agents such as guanidine hydrochloride in the presence of reducing agents such as β-mercaptoethanol or DTT (dithiothreitol).

Under some circumstances, it may be advantageous to incubate the antigen for several hours under conditions suitable for the antigen to undergo a refolding process into a conformation which more closely resembles that of the native antigen. Such conditions generally include low protein concentrations less than 500 μg/ml, low levels of reducing agent, concentrations of urea less than 2 M and often the presence of reagents such as a mixture of reduced and oxidized glutathione which facilitate the interchange of disulphide bonds within the protein molecule.

The refolding process can be monitored, for example, by SDS-PAGE or with antibodies which are specific for the native molecule (which can be obtained from animals vaccinated with the native molecule isolated from parasites). Following refolding, the antigen can then be purified further and separated from the refolding mixture by chromatography on any of several supports including ion exchange resins, gel permeation resins or on a variety of affinity columns.

In yet another embodiment, the expression system used is one driven by the baculovirus polyhedron promoter. The gene encoding the protective antigen can be manipulated by standard techniques in order to facilitate cloning into the baculovirus vector. See Ausubel et al., supra. A preferred baculovirus vector is the pBlueBac vector (Invitrogen, Sorrento, Calif.). The vector carrying the gene for an ilp is transfected into *Spodoptera frugiperda* (Sf9) cells by standard protocols, and the cells are cultured and processed to produce the recombinant antigen.

There also are a variety of eukaryotic vectors that provide a suitable vehicle in which recombinant ilp can be produced. HSV has been used in tissue culture to express a large number of exogenous genes as well as for high level expression of its endogenous genes. For example, the chicken ovalbumin gene has been expressed from HSV using an α promoter. Herz and Roizman (1983). The lacZ gene also has been expressed under a variety of HSV promoters.

In an alternative embodiment, the genes employed may encode antisense oligonucleotides that hybridize, under intracellular conditions, to a target nucleic acid. The target nucleic acid may be a DNA molecule or an RNA molecule. Hybridization results in the inhibition of transcription and or translation of the protein encoded by the target nucleic acid. The design of antisense constructs, based on the sequence of genes, will be evident to those of skill in the art.

The term "antisense nucleic acid" is intended to refer to the oligonucleotides complementary to the base sequences of a target DNA or RNA. Antisense oligonucleotides, when introduced into a target cell, specifically bind to their target nucleic acid and interfere with transcription, RNA processing, transport, translation and/or stability. Targeting double-stranded (ds) DNA with oligos or oligonucleotides leads to triple-helix formation; targeting RNA will lead to double-helix formation.

Antisense constructs may be designed to bind to the promoter and other control regions, exons, introns or even exon-intron boundaries of a gene. Antisense RNA constructs, or DNA encoding such antisense RNA's, may be employed to inhibit gene transcription or translation or both within a host cell, either in vitro or in vivo, such as within a host animal, including a human subject. Nucleic acid sequences which comprise "complementary nucleotides" are those which are capable of base-pairing according to the standard Watson-Crick complementarity rules. That is, that the larger purines will base pair with the smaller pyrimidines to form combinations of guanine paired with cytosine (G:C) and adenine paired with either thymine (A:T), in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

As used herein, the terms "complementary" or "antisense sequences" mean nucleic acid sequences that are substantially complementary over their entire length and have very few base mismatches. For example, nucleic acid sequences of fifteen bases in length may be termed complementary when they have a complementary nucleotide at thirteen or fourteen positions with only a single mismatch. Naturally, nucleic acid sequences which are "completely complementary" will be nucleic acid sequences which are entirely complementary throughout their entire length and have no base mismatches.

Other sequences with lower degrees of homology also are contemplated. For example, an antisense construct which has limited regions of high homology, but also contains a non-homologous region (e.g., a ribozyme) could be designed. These molecules, though having less than 50% homology, would bind to target sequences under appropriate conditions.

While all or part of the IAP-like gene sequence may be employed in the context of antisense construction, statistically, any sequence of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an antisense oligonucleotide to its complementary target increases with increasing length. It is contemplated that antisense oligonucleotides of 8, 9, 10, 11, 12, 13, 14, 15, 16, 17, 18, 19, 20, 25, 30, 35, 40, 45, 50, 60, 70, 80, 90, 100 or more base pairs will be used. One can readily determine whether a given antisense nucleic acid is effective at targeting of the corresponding host cell gene simply by testing the constructs in vitro to determine whether the endogenous gene's function is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

As an alternative to targeted antisense delivery, targeted ribozymes may be used. The term "ribozyme" is refers to an RNA-based enzyme capable of targeting and cleaving particular base sequences in target DNA and RNA. Ribozymes can either be targeted directly to cells, in the form of RNA oligonucleotides incorporating ribozyme sequences, or introduced into the cell as an expression construct encoding the desired ribozymal RNA. Ribozymes may be used and applied in much the same way as described for antisense nucleic acids. Ribozyme sequences also may be modified in much the same way as described for antisense nucleic acids. For example, one could incorporate non-Watson-Crick bases, or make mixed RNA/DNA oligonucleotides, or modify the phosphodiester backbone.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA does not contain any non-coding sequences but, rather, contains only the coding region of the corresponding protein. There may be times when the full or partial genomic sequence is preferred, such as where the non-coding regions are required for optimal expression or where non-coding regions such as introns are to be targeted in an antisense strategy.

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a gene and translation of a RNA into a gene product. In other embodiments, expression only includes transcription of the nucleic acid, i.e., antisense and ribozymes.

In preferred embodiments, the nucleic acid is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter and the Rous sarcoma virus long terminal repeat can be used to obtain high-level expression of transgenes. The use of other viral or mammalian cellular or bacterial phage promoters which are well-known in the art to achieve expression of a transgene is contemplated as well, provided that the levels of expression are sufficient for a given purpose.

By employing a promoter with well-known properties, the level and pattern of expression following transfection can be optimized. For example, selection of a promoter which is active specifically in lung cells, such as tyrosinase (melanoma), alpha-fetoprotein and albumin (liver tumors), CC10 (lung tumor) and prostate-specific antigen (prostate tumor) will permit tissue-specific expression. Further, selection of a promoter that is regulated in response to specific physiologic signals can permit inducible expression. For example, with human PAI-1 promoter, expression is inducible by tumor necrosis factor. Tables 1 and 2 list several elements/promoters which may be employed, in the context of the present invention, to regulate the expression of a transgene. This list is not intended to be exhaustive of all the possible elements involved in the promotion of transgene expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a transgene in an expression construct (Table 2 and Table 3). Additionally any promoter/enhancer combination (as per the Eukaryotic Promoter Data Base EPDB) could also be used to drive expression of a transgene. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

TABLE 2

| PROMOTER |
|---|
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| c-fos |
| c-HA-ras |
| Insulin |
| Neural Cell Adhesion Molecule (NCAM) |
| $\alpha_{1\text{-Anitrypsin}}$ |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

TABLE 3

| Element | Inducer |
|---|---|
| MT II | Phorbol Ester (TPA)<br>Heavy metals |
| MMTV (mouse mammary tumor virus) | Glucocorticoids |
| β-Interferon | poly(rI)X<br>poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |

Where a cDNA insert is employed, one will typically desire to include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal and the bovine growth hormone polyadenylation signal, convenient and known to function well in various target cells. Also contemplated as an element of the expression cassette is a terminator. These elements can serve to enhance message levels and to minimize read through from the cassette into other sequences.

Specific initiation signal also may be required for efficient translation of coding sequences. These signals include the ATG initiation codon and adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements (Bittner et al., 1987).

In preferred embodiments of the invention, the expression construct comprises a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986), adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kilobases of foreign genetic material but can be readily introduced in a variety of cell lines and laboratory animals (Nicolas and Rubenstein, 1988; Temin, 1986).

(i) Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene, termed Ψ, functions as a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a transgene is inserted into the viral genome in the place of certain viral sequences to produce a virus that is replication-defective. In order to produce virions, a packaging cell line containing the gag, pol, and env genes but without the LTR and Ψ components is constructed (Mann et al., 1983). When a recombinant plasmid containing a human cDNA, together with the retroviral LTR and Ψ sequences is introduced into this cell line (by calcium phosphate precipitation for example), the Ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes. Another concern with the use of defective retrovirus vectors is the potential appearance of wild-type replication-competent virus in the packaging cells. This can result from recombination events in which the intact Ψ sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al, 1990).

One limitation to the use of retrovirus vectors in vivo is the limited ability to produce retroviral vector titers greater than $10^6$ infectious U/mL. Titers 10- to 1,000-fold higher are necessary for many in vivo applications.

(ii) Adenovirus

Knowledge of the genetic organization of adenovirus, a 36 kB, linear and double-stranded DNA virus, allows substitution of a large piece of adenoviral DNA with foreign sequences up to 7 kB (Grunhaus and Horwitz, 1992). In contrast to retrovirus, the infection of adenoviral DNA into host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in the human.

Adenovirus is particularly suitable for use as a gene transfer vector because of its mid-sized genome, ease of manipulation, high titer, wide target-cell range, and high infectivity. Both ends of the viral genome contain 100–200 base pair (bp) inverted terminal repeats (ITR), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and all the mRNAs issued from this promoter possess a 5' tripartite leader (TL) sequence which makes them preferred mRNAs for translation.

In the current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure. Use of the YAC system is an alternative approach for the production of recombinant adenovirus.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham, et al., 1977). Since the E3 region is dispensable from the adenovirus genome (Jones and Shenk, 1978), the current adenovirus vectors, with the help of 293 cells, carry foreign DNA in either the E1, the E3 or both regions (Graham and Prevec, 1991). In nature, adenovirus can package approximately 105% of the wild-type genome (Ghosh-Choudhury, et al., 1987), providing capacity for about 2 extra kB of DNA.

Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1 deleted virus is incomplete. For example, leakage of viral gene expression has been observed with the currently available adenovirus vectors at high multiplicities of infection (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the method of the present invention. This is because Adenovirus type 5 is a human adenovirus about which a great deal of biochemical and genetic information is known, and it has historically been used for most constructions employing adenovirus as a vector.

As stated above, the typical adenoviral vector according to the present invention is replication defective and will not have an adenovirus E1 region. Thus, it will be most convenient to introduce the transgene nucleic acid into the position from which the E1 coding sequences have been removed. However, the position of insertion of the coding region within the adenovirus sequences is not critical to the present invention. The nucleic acid encoding a transcription unit also may be inserted in lieu of the deleted E3 region in E3 replacement vectors as described previously by Karlsson et. al. (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$\mathbf{10}^{11}$ plaque-forming unit (PFU)/ml, and they are highly infective. The life cycle of adenovirus does not require integration into the host cell genome. The foreign genes delivered by adenovirus vectors are episomal, and therefore, have low genotoxicity to host cells. No side effects have been reported in studies of vaccination with wild-type adenovirus (Couch et al., 1963; Top et aL, 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Experiments in administering recombinant adenovirus to different tissues include trachea instillation (Rosenfeld et al., 1991; Rosenfeld et al., 1992), muscle injection (Ragot et al., 1993), peripheral intravenous injection (Herz and Gerard, 1993), and stereotactic inoculation into the brain (Le Gal La Salle et al., 1993). In addition to these protocols, the present invention also contemplates direct tumoral injection.

(iii) Other Viral Vectors as Expression Constructs

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

IV. Antibodies to IAP-Like Proteins

Antibodies against IAP-like proteins will be useful in the present invention, primarily in assays for the detection of these protein. Means for preparing and characterizing antibodies are well known in the art (see, e.g., Antibodies: A Laboratory Manual, Cold Spring Harbor Laboratory, 1988; incorporated herein by reference).

Methods for generating polyclonal antibodies (Mabs) begin by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat.

Immunogenic composition of the invention include IAP-like proteins, derivatives or fragments and the like. As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a compound to a carrier protein are well known in the art and include glutaraldehyde, m-maleimidobencoyl-N-hydroxysuccinimide ester, carbodiimyde and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed Mycobacterium tuberculosis), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and tittering is repeated until a suitable titer is achieved. When a desired level of immunogenicity is obtained, the immunized animal can be bled and the serum isolated and stored, and/or the animal can be used to generate MAbs.

MAbs may be readily prepared through use of well-known techniques, such as those exemplified in U.S. Pat.

No. 4,196,265, incorporated herein by reference. Typically, this technique involves immunizing a suitable animal with a selected immunogen composition, e.g., a purified or partially purified protein, polypeptide or peptide. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986, pp. 60–61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5\times10^7$ to $2\times10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). cites). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71–74, 1986).

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid. Radioimmunoassays, enzyme immunoassays, cytotoxicity assays, plaque assays, dot immunobinding assays, and the like, may be used.

Where one desires to generate an anti-IAP-like protein antibody with defined activity, one would generally screen the candidate hybridomas to identify those hybridomas that produce antibodies that have the desired inhibitory or stimulatory properties. Any selected hybridomas would then be serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

V. Methods for the Inhibition of Apoptosis

In one embodiment of the present invention, there is provided methods for the inhibition of apoptosis in a cell. This is particularly useful where one seeks to immortalize a cell or, at a minimum, increase the longevity of a cell. This permits one to maintain that cell in culture for extended periods of time, perhaps indefinitely. Immortalized cells are useful primarily as factories for production of proteins of interest, but it may be important to immortalize cell simply so that they may be studied in vitro with greater ease.

The general approach to inhibiting apoptosis according to the present invention will be to provide a cell with an ilp, thereby permitting the inhibitory activity of the ilp to take effect. While it is conceivable that the protein may be delivered directly, a preferred embodiment involves providing a nucleic acid encoding an ilp to the cell. Following this provision, the ilp protein is synthesized by the host cell's transcriptional and translational machinery. Cis-acting regulatory elements necessary to support the expression of the ilp gene will be provided, as described above, in the form of an expression construct. It also is possible that the expression of an endogenous ilp could be stimulated, thereby achieving the same or similar effect.

In order to effect expression of constructs encoding ilp genes, the expression construct must be delivered into a cell. As described above in discussing viral vectors, the one mechanism for delivery is via viral infection, where the expression construct is encapsidated in an infectious viral particle. Such suitable viruses include herpesviruses, retroviruses, adenoviruses, adeno-associated viruses and vaccinia viruses. Viral vectors further may be modified to enhance their uptake by host cells.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use, as discussed below.

In one embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro, but it may be applied to in vivo use as well.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In other embodiments, the delivery vehicle may comprise a ligand and a liposome. Where a bacterial promoter is employed in the DNA construct, it also will be desirable to include within the liposome an appropriate bacterial polymerase.

Other expression constructs which can be employed to deliver a nucleic acid encoding an IAP-like transgene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994). Mannose can be used to target the mannose receptor on liver cells. Also, antibodies to CD5 (CLL), CD22 (lymphoma), CD25 (T-cell leukemia) and MAA (melanoma) can similarly be used as targeting moieties. In other embodiments, the delivery vehicle may comprise a ligand and a liposome.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, 3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, the herpes simplex virus thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon (Phillips et al., 1985; Mizrahi, 1983). Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

VI. Methods for the Induction of Apoptosis

In another embodiment of the present invention, there is contemplated the method of inducing apoptosis in cells that have lost their normal growth regulatory control. The primary manner in which this aspect of the invention will be employed is in the treatment of cells, in vivo or ex vivo, that have lost the ability to undergo normal programmed cell death. Typically, these cells are cancer cells. It is contemplated that a variety of different cancers will be susceptible to this treatment. For example, the cancer cell may be lymphoma, melanoma, sarcoma, leukemia, retinoblastoma, hepatoma, myeloma, glioma, mesothelioma or carcinoma cell.

The general form that this aspect of the invention will take is the provision, to a cell, of an agent that will inhibit ilp function. Three such agents are contemplated. First, one may employ an antisense nucleic acid that will hybridize either to the ilp gene or the ilp transcription, thereby preventing transcription or translation, respectively. The considerations relevant to the design of antisense constructs have been presented above. Second, one may utilize an ilp-binding protein, for example, an antibody that binds immunologically to an ilp, the binding of which will block or reduce the activity of an ilp. Third, one may provide to the cell an antagonist of ilp. A discussion of the methods for antibody production and their selection have been presented above, and a discussion of the delivery of pharmaceuticals is presented below.

Many of the gene transfer techniques that generally are applied in vitro can be adapted for ex vivo or in vivo use. For example, selected organs including the liver, skin, and muscle tissue of rats and mice have been bombarded in vivo (Yang et al., 1990; Zelenin et al., 1991). Naked DNA also has been used in clinical settings to effect gene therapy. These approaches may require surgical exposure of the tumor tissue or direct intratumoral injection. Nicolau et al. (1987) accomplished successful liposome-mediated gene transfer in rats after intravenous injection.

Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. Thus, it is envisioned that DNA encoding an antisense construct also may be transferred in a similar manner in vivo.

In certain embodiments of clinical treatment, gene transfer may more easily be performed under ex vivo conditions. Ex vivo gene therapy refers to the isolation of cells from an animal, the delivery of a nucleic acid into the cells, in vitro, and then the return of the modified cells back into an animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods.

During in vitro culture conditions, the expression construct is delivered to the host cell and the protein is expressed. Finally, the cells may be reintroduced into the original animal, or administered into a distinct animal, in a pharmaceutically acceptable form by any of the means described below. Thus, providing an ex vivo method of treating a mammal with a pathologic condition is within the scope of the invention.

Where the embodiment involves the use of an antibody that recognizes an ilp, consideration must be given to the mechanism by which the antibody is introduced into the cell cytoplasm. This can be accomplished, for example, by providing an expression construct that encodes a single-chain antibody version of the antibody to be provided. Most of the discussion above relating to expression constructions for antisense versions of ilp's will be relevant to this aspect of the invention. Alternatively, it is possible to present a bifunctional antibody, where one antigen binding arm of the antibody recognizes for an ilp and the other antigen binding arm recognizes a receptor on the surface of the cell to be targeted. Examples of suitable receptors would be any tumor specific marker, such as CEA. Alternatively, it may be possible to use receptors also present on normal cells, given the assumption that the existence of an ilp-binding antibody in a normal cell will not result in any adverse effect on the normal cell.

The method by which the DNA or antibody is transferred, along with the preferred delivery route, will be selected based on the particular cancer to be treated. Those of skill in the art are capable of determining the most appropriate methods based on the relevant clinical considerations.

The foregoing approaches to the treatment of cancer may be combined with more traditional chemo- or radiotherapeutic regimens. For example, the following chemotherapeutic agents may be used: cisplatin (CDDP), carboplatin, procarbazine, nitrosourea, mechlorethamine, cyclophosphamide, ifosfamide, melphalan, chlorambucil, bisulfan, nitrosurea, dactinomycin, daunorubicin, doxorubicin, bleomycin, plicomycin, mitomycin, taxol, vincristin, vinblastine, lomustine, TNF and etoposide (VP16).

Radiation therapy transfers discrete energy units, called photons, to tissues causing damage to both normal and malignant cells. Ionizing irradiation stimulates production of oxygen free radicals which react with macromolecules and induces DNA damage (Cole et al., 1980). "Early" radiation effects include damage to proliferating cells, while "late" effects involve cell death and affect many different kinds of cells. Fortunately, radiation exploits the differential effects on malignant versus non-malignant cells, namely, that rapidly proliferating cells undergoing significant DNA synthesis suffer more severe effects from the DNA damage induced by radiation.

The dose of radiation is dependent upon tissue and tumor type. The treatment is usually fractionated to prevent toxicity and can be in the 1–5 Grey range over a several week period. For the treatment of rectal cancer radiation, 45 Grey total dose is given (1.8 Grey dose/day, Monday through Friday). For the enhancement of gene expression, a single dose of between 1 and 8 Grey is contemplated for gamma radiation.

VII. Methods for the Inhibition of Cysteine Proteases

The present invention also encompasses the use of ilp and genes coding therefor to inhibit the activation of cysteine proteases, such as ICE protease. In addition, increasing the expression of an endogenous ilp also is contemplated to be useful in this aspect of the invention. For the ICE protease to be enzymatically active, the 45 kD pro-ICE precursor peptide most be processed into two subunits, p20 and p10. In vivo, this cleavage can be carried out by active ICE itself or by other members of the ICE protease family. The data presented below show that ilp's prevent this activation. This is significant in that many biologically active polypeptides are substrates for the ICE proteases, and inhibition of ICE proteases will lead to the regulation of the biological activity associated with these polypeptides. For example, IL-1β, which mediates inflammatory responses in vivo, is activated the ICE protease. Prevention of IL-1β activation could have profound effects on the inflammatory response in vivo. The delivery of ilp's and genes coding therefore, both in vitro and in vivo, are addressed elsewhere in this document and need not be repeated here.

VIII. Methods for the Inhibition of Virus-Induced Cell Death

Another embodiment of the present invention, there are provided methods for the inhibition of virus-induced cell death comprising the provision of ilp or genes coding therefor. Also contemplated in this aspect of the invention is the stimulation of endogenous ilp. Though this mechanism is generally thought of as advantageous only to the virus, certain scenarios arise in which it will be desirable to effect this results for other reasons. For example, in the production of virus stocks, it is desirable that the highest possible titer be achieved. By preventing early death of the cell, ilp's can extend the productive life of a virally-infected cell and, thereby, increase the titer of the virus stock produced. Where viruses are used as therapeutic vectors (adenovirus, AAV, retrovirus, HSV), the ability to increase titer may mean the difference between an effective and an ineffective pharmaceutical. It also is conceivable that ilp's could be used therapeutically to prevent the death of cells infected with viruses. One example where this method could be applied would be the elimination of T-helper cells in HIV infections. By curbing the HIV-induced reduction in T-helper cells, ilp genes might extend the life of the HIV+ patient. The delivery of ilp's and genes coding therefore are addressed elsewhere in this document and need not be repeated here.

IX. Pharmaceuticals and In vivo Methods for the Treatment of Disease

Aqueous pharmaceutical compositions of the present invention will have an effective amount of an antisense ilp construct or a protein that inhibits ilp function, such as an anti-ilp antibody. Such compositions will generally be dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as those for intravenous or intramuscular injection, other pharmaceutically acceptable forms include, e.g., tablets or other solids for oral administration; time release capsules; and any other form currently used, including cremes, lotions, mouthwashes, inhalants and the like.

The active compounds of the present invention will often be formulated for parenteral administration, e.g., formulated for injection via the intravenous, intramuscular, subcutaneous, or even intraperitoneal routes. The preparation of an aqueous composition that contains glycosylceramide synthesis inhibitory compounds alone or in combination with a chemotherapeutic agent as active ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in cremes and lotions. These forms may be used for treating skin-associated diseases, such as various sarcomas.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

X. EXAMPLES

The following examples are included to demonstrate preferred embodiments of the present invention. It should be appreciated by those of skill in the art that that techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar results without departing from the spirit and scope of the invention.

Example 1

Materials and Methods

Cell Culture

N18 (mouse neuroblastoma), BHK (baby hamster kidney), and 293 (human embryonic kidney) cells were maintained in Dulbecco's Modified Eagle's Medium (DMEM) with 10% fetal bovine serum, 2 mM glutamine, 100 units/ml penicillin and 100 μg/ml streptomycin, and maintained at 37° C. in 5% C02. 293 cells were transfected by calcium phosphate as previously described (Perkins et al., 1994) Staining of cells for β-galactosidase activity and viability analysis was performed as described previously (Miura et al., 1993)

Recombinant Viruses

The Sindbis virus vector was generated from plasmids TE12 (nucleotides 1–10,381; 11,382–13637) and TZJSINC (nucleotides 10,382–11,485) (Hertz and Huang, 1992; Lustig et al., 1988) with a BstE II restriction site inserted at the junction between nucleotide 11,485 of TZJSINC and nucleotide 11,382 of TE12. The resulting construct contains a cDNA of the Sindbis virus genome with a duplicated copy of a viral subgenomic promoter and a unique BstE II restriction site inserted between the viral coding sequences and the 3' untranslated/regulatory sequences of the Sindbis virus genome. The baculovirus Op-iap gene (Birnbaum et al., 1994), the human bcl-$x_L$ cDNA (Boise et al., 1993), and the bacterial chloramphenicol acetyltransferase gene (CAT) (Gorman et al., 1982) gene were cloned into the virus vector as PCR products with flanking BstE II sites. To generate the Op-iap/stop and bcl-$x_L$/stop viruses, a nonsense oligonucleotide containing stop codons in all three reading frames was inserted after codon 8 (AscIsite) in the wild-type Op-iap virus construct or after codon 78 (SmaI site) in the wild-type bcl-$x_L$ virus construct.

Viral RNA was transcribed in vitro from approximately 400 ng of linearized plasmid DNA using SP6 RNA polymerase. Ten microliters of the 25 μl total transcription reaction was transfected into BHK cells with 30 μl lipofectin (Gibco/BRL) according to the manufacturer's instructions. The culture medium containing infectious recombinant virus was collected 24 h after transfection and stored at −80° C. Virus titers were determined according to established protocols. Cells were infected with recombinant viruses at a multiplicity of infection of 5 plaque forming units/cell in culture medium containing 1% serum for 1 h. After infection cells were returned to medium containing 10% serum, and cell viability was determined approximately 48 h later by trypan blue exclusion.

DNA and Protein Sequence Analysis

The Drosophila ilp gene was originally identified in the Genbank/EMBL nucleotide databases (accession #M96581) by a search for potential iap homologs to Op-iap using the TFASTA sequence comparison program (Genetics Computer Group, University of Wisconsin). Having characterized full-length cDNAs containing the Drosophila ilp gene (see below), the predicted amino acid sequence of this gene was used to search the human STS and EST DNA databases. This search revealed that an 81 bp sequence within a 273 bp STS sequence (accession #L24579) potentially encoded an iap-like RING finger domain, and this sequence was used to identify full-length cDNA clones as described below.

Additional DNA and protein sequence analysis was performed using the FASTA, BLAST, WORDSEARCH, PEPTIDESORT, and BESTFIT programs contained within the GCG package. DNA sequencing was facilitated using the sequence project management programs contained within the DNASTAR package (DNASTAR, Madison, Wis.). Additional searches were performed at the National Center for Biotechnology Information internet site.

Molecular Cloning of Drosophila and Human ilp

The polymerase chain reaction (PCR) was performed under standard conditions using Amplitaq DNA polymerase (Chiron) to amplify a ~580 bp fragment from cDNA prepared from Schneider SC2 Drosophila cells, using the oligonucleotide primers 5'ATGGCCCCTGAATGC-CCCAGTTTCCGCGGAGGATCTG3' (SEQ ID NO:53) and 5'CATCACGCCGCAGGCTCTGGCAAAG-GCAGGTTTC3' (SEQ ID NO: 54), which are specific to a region predicted to encompass a BIR element as judged by the computer analysis described above. This fragment was subcloned into PCRscript (Stratagene) and subsequently used as a probe to isolate full-length clones from a λgt10 adult Drosophila cDNA library (Clontech).

Fragments containing a segment of the human ilp gene were isolated with a nested PCR approach using plasmid DNA from a human B cell two-hybrid cDNA library (Clontech) as a template. An initial PCR reaction was performed for 30 cycles under standard conditions using Amplitaq DNA polymerase with the human STS-specific primer 5' AGTAATGACTGTGTAGCACATGGCACAC 3'(SEQ ID NO:55) and the library-specific primer 5'GCG-TATAACGCGTTTGGAATCACTACAGGGATG 3' (SEQ ID NO:56). One microliter from this reaction was used as a template for a second 30-cycle PCR reaction with the STS-specific nested primer 5'TCAACTGCTTCAGCACAT-TGTTTTACAAGTGAC 3' (SEQ ID NO:57) and the library-specific nested primer 5'TTTAATACCACTA-CAATGGATGATGTATATAAC 3' (SEQ ID NO:58). The resulting ~600 bp fragment was subcloned into PCRscript, and subsequently used as a probe to isolate full-length clones from a human fetal heart λgt10 cDNA library (Clontech).

Full-length clones containing the Drosophila and human ilp genes were isolated from cDNA libraries essentially following the manufacturer's recommendations (Clontech). Insert DNA from phage clones was excised with EcoR I and subcloned into Bluescript II SK+ (Stratagene), and sequenced by the dideoxy method using Sequenase (United States Biochemical) using the modifications described by Hsiao (Hsiao, 1991). Both the Drosophila and human ilp sequences have been deposited in Genbank with accession numbers U32373 and U32974, respectively. The additional human iap-related EST sequences referred to in this application have the following GenBank accession numbers: R07927, R57975, R19628, T96284, and T16094.

Northern Blot Analysis

The same $^{32}$P-labeled DNA fragments described above were used to probe Northern blots. Human Multiple Tissue Northern (MTN) blots were probed at high stringency following the supplier's instructions (Clontech). Embryonic, larval, and adult poly(A)+ RNA from *Drosophila melanogaster* (Clontech) was used to prepare a Northern blot as described previously (June et al., 1987), which was probed at high stringency.

Immunofluorescence Studies 293 cells ($5\times10^4$) were plated directly onto Lab-Tek chamber slides (Nunc), transfected with 200 ng plasmid DNA by calcium phosphate, and maintained for 48 h. All subsequent procedures were performed at room temperature. Cells were washed once with 0.5 ml phosphate buffered saline (PBS) and fixed in 2% paraformaldehyde (0.4 ml) for 10 min. Fixed cells were washed once in PBS containing 0.03% saponin (0.5 ml), and permeabilized in PBS containing 0.1% saponin for 15 min. Blocking was performed by incubation in the same solution containing 20% goat serum for 15 min, followed by addition of 0.4 ml of a solution containing 10 μg/ml of anti-Myc monoclonal antibody (clone 9E10, Pharmingen), 1% bovine serum albumin (BSA), 0.01% sodium azide and 0.1% saponin in PBS for 30 min. Slides were washed twice in PBS/0.03% saponin, and incubated with secondary antibody (FITC-conjugated goat anti-mouse, 1/50 dilution, Sigma) was performed for 30 min in the same PBS/BSA/azide/saponin solution. Cells were washed twice in PBS/0.03% saponin and visualized by epifluorescence microscopy using a Leitz DM-RB microscope with a Nikon 6006 camera.

Expression Vectors

The human ilp gene, and the crmA gene were subcloned into the pcDNA3 mammalian expression vector (Invitrogen). To construct the epitope-tagged human ilp construct, site-directed mutagenesis was performed on human ilp in Bluescript SK+ to add the 9E10 Myc epitope (EQLISEEDL) to the predicted amino terminus of the protein. This modified sequence was subsequently cloned into pcDNA3. The Op-iap gene was subcloned into a modified Rous sarcoma virus expression (Duckett et al., 1993). The construction of the pactβgal' and pβactM10Z plasmids has previously been described (Miura et al., 1993).

In vitro Translation

One microgram aliquots of the relevant iap-related cDNAs were used to program TNT rabbit reticulocyte lysates (Promega) for coupled transcription-translation reactions according to the manufacturers instructions. Aliquots were resolved on 9.5% SDS-polyacrylamide gels, fluorographed using Enhance (DuPont) and products visualized by autoradiography.

Example 2

Results

Baculovirus IAP Protein Can Protect Mammalian Cells from Cell Death

Figure 1B:
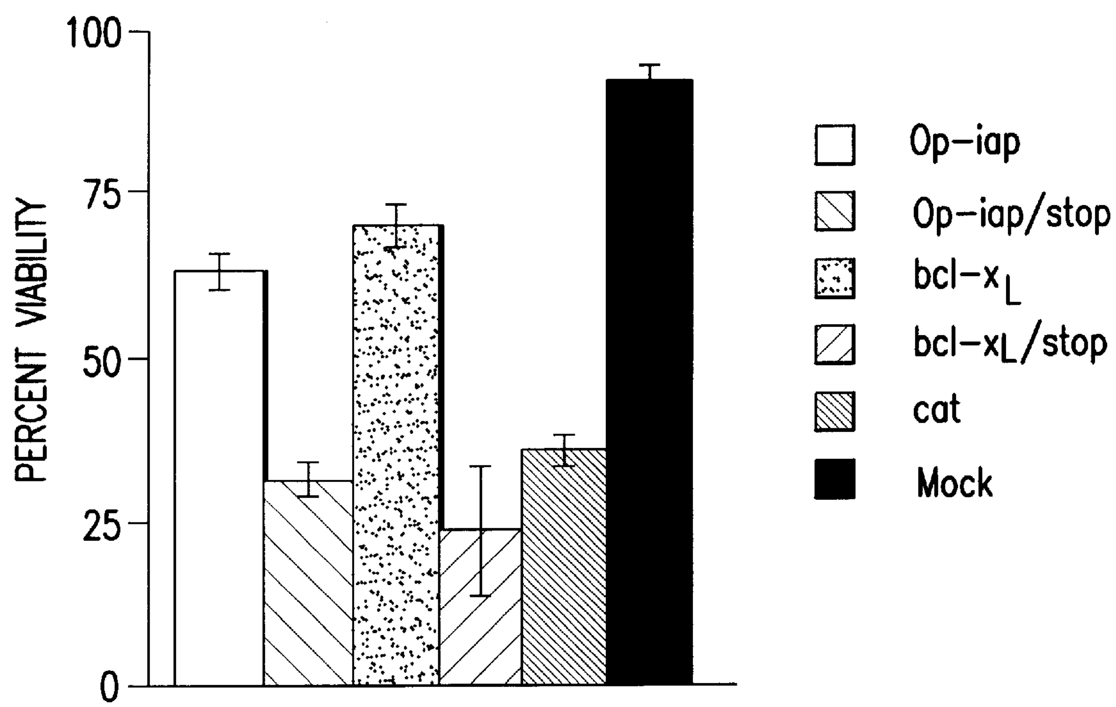

Previous experiments have demonstrated that overexpression of the iap gene from the baculovirus *Orgyia pseudotsugata* nuclear polyhedrosis virus (Op-iap) can inhibit cell death induced by baculovirus infection in *Spodoptera frugiperda* cells (Clem et al., 1991; Clem and Miller, 1993; Crook et al., 1993; Birnbaum et al., 1994; Clem and Miller, 1994b). To determine whether iap overexpression can confer protection in mammalian cells, the full-length Op-iap gene (Op-iap), or a mutant gene containing a premature stop codon (Op-iap/stop), were introduced into a Sindbis virus vector and expressed under the control of a duplicated copy of a late viral subgenomic promoter (Hertz and Huang, 1992). The resulting viruses were then tested for their ability to induce cytopathic effects in target cells permissive for Sindbis virus infection (Lustig et al., 1988). Cells infected by Sindbis virus rapidly undergo apoptosis unless a cell survival gene such as bcl-2 is introduced into the virus (Levine et al., 1993). Viability of baby hamster kidney (BHK) cells (FIG. 1A) and N18 mouse neuroblastoma cells (FIG. 1B) infected with viruses containing wild-type Op-iap was significantly greater than that of cells infected with the viral vector alone or viruses containing an Op-iap gene with a premature stop codon. This protection was similar to that conferred by inclusion of the cell survival gene bcl-$x_L$ in the recombinant virus. Bcl-$x_L$-mediated protection was also inhibited by the introduction of a premature stop codon. These observations suggest that iap inhibits cell death by modulating an evolutionarily conserved step in apoptosis.

Molecular Cloning of Drosophila and Human Homologs of Baculovirus iap

Figure 2A:
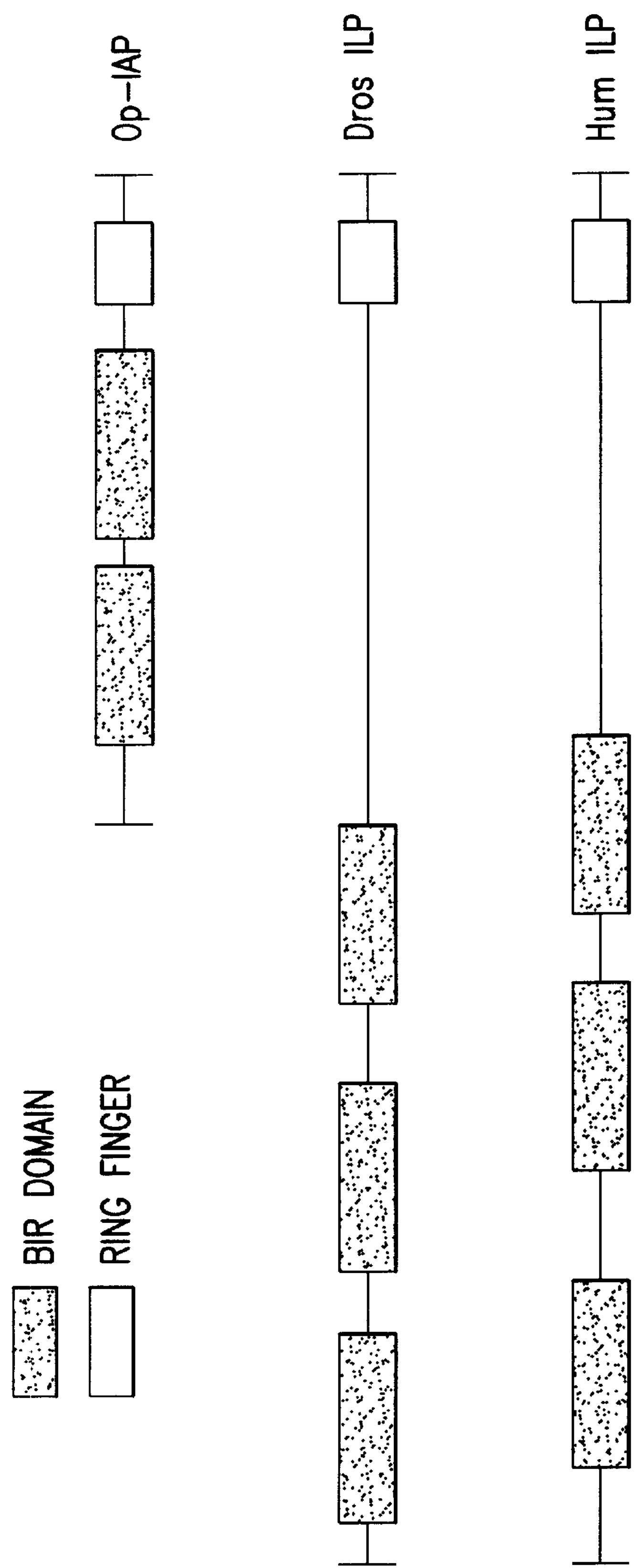

The demonstration that Op-iap can protect mammalian cells from virus-induced cell death suggested that it may be a viral homolog of an evolutionarily conserved gene(s) involved in the control of programmed cell death. In a search of the nucleotide databases, an open-reading frame with homology to Op-IAP was identified within a 5,307 bp *Drosophila melanogaster* genomic sequence that had been isolated from region 52D of the Drosophila genome (Ross et al., 1994). To determine whether this region encodes an IAP-like protein, we used the polymerase chain reaction (PCR) to amplify a 580 bp fragment from cDNA prepared from Drosophila SC2 cells. Sequence analysis of this fragment confirmed that it encoded an in-frame IAP homolog. To obtain full-length cDNAs, a DNA fragment derived from the original PCR product was used to screen a cDNA library prepared from adult Drosophila RNA. Several independent cDNAs were isolated, and a single open-reading frame was identified (FIG. 2B, SEQ ID NO:1). In the longest cDNA, stop codons in all three reading frames were identified 5' of a potential initiator methionine. Sequences around the initiator methionine conformed to the consensus initiation codon in Drosophila (Cavener and Ray, 1991). Comparison of the Drosophila ilp open-reading frame, which we have termed IAP-like protein (dILP), to the baculovirus IAP sequence revealed that the carboxy-terminal ends of both proteins contained a highly conserved RING finger domain (55% amino acid identity over 38 residues).

By comparing Drosophila ilp to baculovirus iap sequences, highly conserved regions were identified and used to search nucleotide databases for potential mammalian homologs. A 273 bp sequence tag site (STS) which mapped to the q24–25 region of the human X chromosome was identified which contained an 81 bp fragment with a predicted amino acid sequence of greater similarity to the RING finger of dILP and Op-IAP than the RING fingers contained in other known proteins. In order to determine whether this sequence was contained within an open-reading frame which encodes an IAP-like protein, a nested PCR strategy, using oligonucleotide primers to this fragment as well as primers complementary to regions of the cloning sites contained within several cDNA libraries, was designed. PCR products isolated from these libraries, when sequenced, revealed the presence of in-frame BIR repeats upstream of the RING finger domain. cDNA clones encoding the full-length human IAP were subsequently isolated from a human fetal heart cDNA library (FIG. 2C, SEQ ID NO:2).

Interestingly, the amino termini of dILP and HILP are predicted to contain three BIR motifs, while the baculovirus IAP proteins contain only two. One additional difference between the two proteins is that in the cellular proteins, the BIR domains are separated from the RING finger by an amphipathic region of 120 to 170 amino acids. This region is absent in baculovirus IAP proteins.

Properties of Cellular IAP-like Proteins

The predicted overall structures of dILP and hILP are very similar. Both proteins contain three BIR elements and a highly conserved carboxy-terminal RING finger domain (FIG. 3A, SEQ ID NO:3–25; FIG. 3B, SEQ ID NO:26–52). Both proteins are 497 amino acids in length and the calculated molecular weights of dILP and hILP are 54 kD and 57 kD, respectively. Both dilp and hilp appear to be widely expressed at the mRNA level. dilp mRNA was found to be expressed at high levels in larval, embryonic, and adult Drosophila mRNAs. Similarly, RNA transcripts for hilp were detected in all tissues and cell lines tested. Thus, the ilp genes appear to be expressed throughout Drosophila development and in a wide variety of mammalian tissues.

To characterize the subcellular distribution of hILP, an expression plasmid encoding an epitope-tagged version of hILP was produced. This expression plasmid was transiently transfected into the 293 human embryonic kidney cell line, and the transfected protein was localized by staining with an epitope-specific monoclonal antibody. These experiments revealed that hILP-staining could be detected diffusely throughout the cytoplasm of cells. No evidence for accumulation of the protein in proximity to organelles or within the nucleus was seen. Like a number of other evolutionarily conserved regulators of apoptosis, hILP appears to be primarily a cytoplasmic protein.

Both dILP and hILP were found to contain three copies of the BIR motifs originally identified at the amino terminus of viral iap genes. In addition to the viral iap genes, one other gene has been reported to contain BIR repeats, the human neural apoptosis inhibitory protein (NAIP) gene (Roy et al., 1995). NAIP is partially deleted in the majority of individuals with spinal muscular atrophy. Sequence comparisons between dilp, hilp, and NAIP revealed a previously unrecognized third copy of a BIR repeat at the amino terminus of NAIP. Thus NAIP, like dILP and hILP, contains three copies of the BIR motif at its amino-terminus. Alignment of the BIR repeats from viral IAP, dILP, hILP, and NAIP reveal that each BIR motif within these proteins is almost equally related to the BIR domains within the same protein and to the BIR domains within the other proteins (FIG. 3A, SEQ ID NO:3–25). A consensus amino acid sequence for a BIR domain is discernible from this alignment. It also appears that the carboxy terminal half of a BIR domain has a primary amino acid sequence suggestive of a zinc finger with a $CX_2CX_{16}HX_6C$ spacing.

The carboxy-terminal domains of Op-IAP, dILP, and hILP each encode highly related RING finger domains. Such a domain is lacking from NAIP. Although each of the iap-related genes contain cysteine and histidine residues spaced at intervals which are characteristic of a RING finger domain, the RING fingers of Op-IAP, dILP, and hILP are more closely related to each other than they are to RING finger domains contained within a variety of other proteins (FIG. 3B, SEQ ID NO:26–52). This degree of evolutionary conservation suggests that dilp and hilp may be true cellular homologs of the viral iap genes. However, Southern blot analysis revealed the presence of several hilp-related sequences within the human genome (data not shown). Consistent with this, a search of the expressed sequence tag (EST) databases revealed the presence of at least five additional ESTs which encode proteins containing BIR domains and/or IAP-like RING finger domains. Thus, hilp may be only one of several human genes related to the viral iap genes.

hilp Can Protect Transfected Cells from Apoptosis

Figure 4:
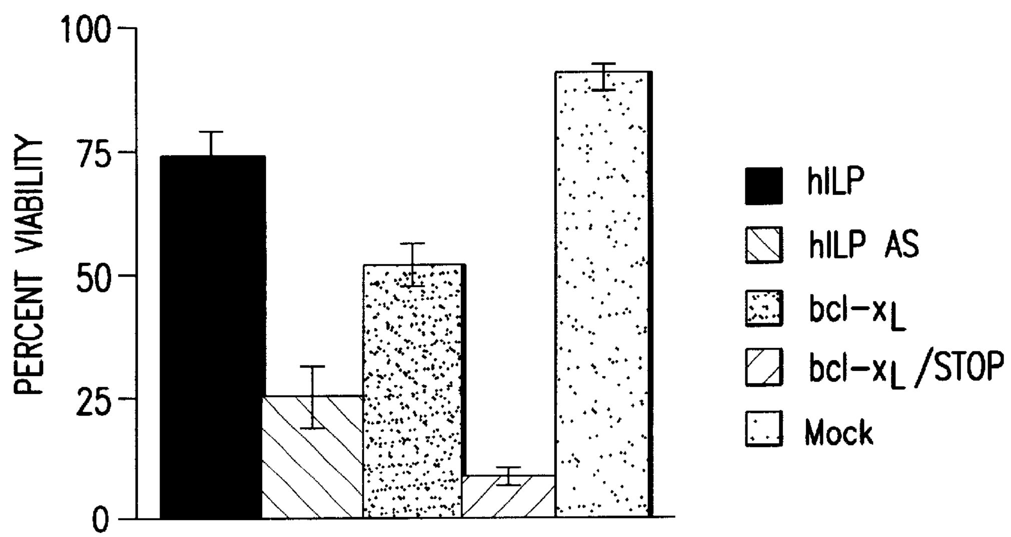
FIG. 4: Protection of cells from Sindbis virus-induced apoptosis by hilp. BHK cells were infected with recombinant Sindbis viruses containing human ilp (hilp); an antisense hilp (hilp AS), bcl-$x_L$ or a bcl-$x_L$ gene containing a stop codon (bcl-$x_L$/stop) as described in the legend to FIG. 1. Cell viabilities 48 hrs post infection are shown (mean and standard error). Data are representative of eleven independent experiments.

Given the striking similarity in overall organization and primary amino acid sequence between viral IAP and the cellular IAP proteins, we have investigated the ability of hilp to protect cells from apoptosis. Recombinant Sindbis viruses were generated containing the hilp gene or an antisense control, and these viruses were assayed for their cytopathic effects on BHK cells (FIG. 4). Following infection, the viability of cells infected with the ilp-expressing virus was significantly higher than the viability of cells infected with the control virus. These data suggest that, like Op-IAP, hILP can suppress cell death induced in response to viral infection.

Figure 5:
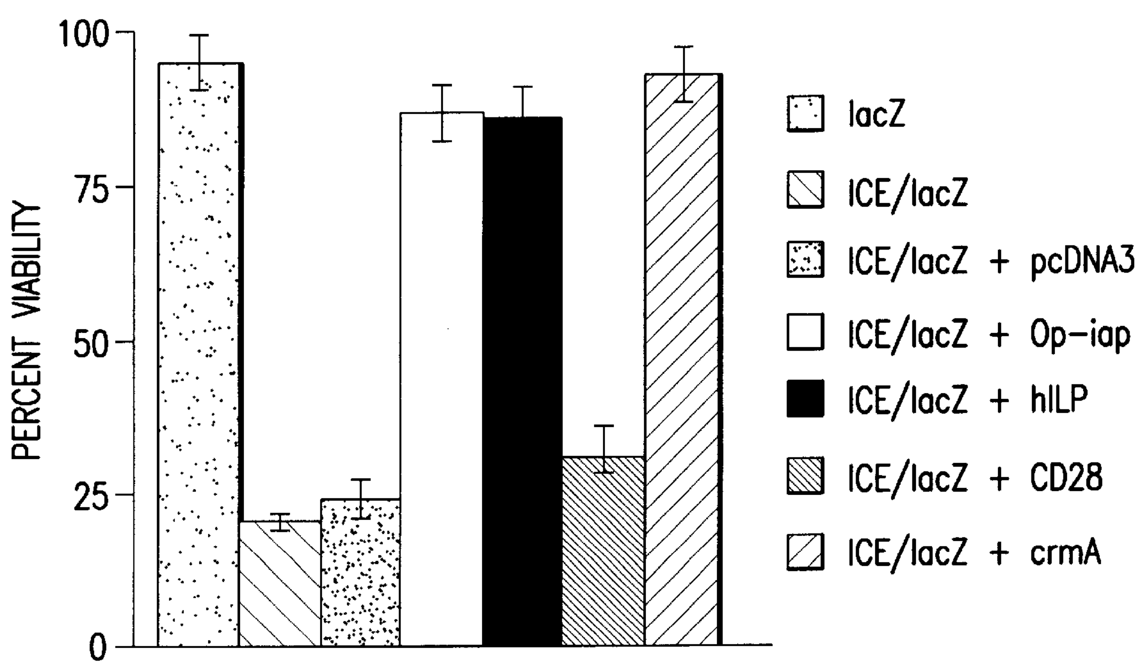
FIG. 5: Both iap and hilp protect cells from ICE-induced apoptosis. $1\times10^4$ 293 cells were transfected with plasmids encoding either a lacZ gene or a pro-ICE/lacZ fusion gene. In each case indicated, cells were cotransfected either with a control plasmid or plasmids expressing crmA, Op-iap, or hilp. Data are expressed as mean and standard deviation of triplicate cultures and are representative of four independent experiments.

To independently verify the ability of Op-IAP and hILP to prevent programmed cell death, the effect of these genes on ICE-induced death was examined. It has previously been demonstrated that mammalian cells can be induced to undergo apoptosis in response to transient transfection of an expression plasmid containing the pro-ICE protease fused to the *E. coli* lacZ gene (Miura et al., 1993). This system provides a reproducible method for assessing the role of individual genes in protecting cells from apoptotic cell death. The 293 cell line was transiently transfected with either the ICE/lacZ plasmid, pβactM10Z, which contains pro-ICE fused to lacZ, or the lacZ plasmid, pactβgal', which contains only the lacZ gene (Miura et al., 1993; Wang et al., 1994) in combination with various control and test plasmids. Transient transfection of the ICE/lacZ plasmid resulted in programmed cell death of over half the cells within 18 hours of transfection (FIG. 5). Cell death of the transfected cells was readily discernible following the addition of X-gal solution to develop the color reaction. Viable blue cells are flat, well-spread cells with easily discernible nuclei. In contrast, apoptotic cells are smaller, round cells with condensed and often misshapen nuclei. As has been reported (Miura et al., 1993; Wang et al., 1994), cell death induced by ICE/lacZ was inhibited by co-transfection with a plasmid containing crmA (FIG. 5). In contrast, cotransfection of ICE/lacZ with a control expression plasmid encoding an irrelevant gene, the CD28 surface antigen, had no effect on the overall cell death. To test the ability of hilp to protect cells from transfection of the pro-ICE construct, the hilp gene was cloned into the pcDNA3 expression plasmid. In vitro transcription and translation verified the resulting plasmid was capable of producing a full-length hILP protein. Cotransfection of either the hilp or Op-iap plasmid protected ICE/lacZ -transfected cells nearly as well as cotransfection of the crmA gene. These data demonstrate that the viral iap gene's ability to protect mammalian cells from cell death is not restricted to apoptosis induced by viral infection, and also demonstrates that both the human ilp and viral iap genes can protect cells from apoptotic stimuli.

XI. REFERENCES

The following references, to the extent that they provide exemplary procedural details or other information supplementary to that set forth herein, are incorporated by reference:

Antibodies. A Laboratory Manual, Cold Spring Harbor Laboratory, 1988.

Baichwal and Sugden, In: Kucherlapati R, ed. Gene transfer. New York: Plenum Press, pp. 117–148, 1986.

Beidler et al., *J. Biol. Chem.,* 270:16526–16528, 1995.

Benvenisty and Neshif, *Proc. Nat'l Acad. Sci. USA,* 83:9551–9555, 1986.

Birnbaum et al., *J. Virology* 68:2521–2528, 1994.

Bishop, *Cell,* 64:235–248, 1991.

Bittner et al., *Methods in Enzymol.,* 153:516–544, 1987.

Blake et al., *Oncogene,* 6:653–657, 1991.

Boise et al, *Cell,* 74:597–608, 1993.

Borden et al., *EMBO J.,* 14:1532–1541, 1995.

Bradford, *Anal. Biochem.* 72:248–254 (1976).

Brutlag, et al., *CABIOS* 6:237–245, 1990.

Bump et al, *Science,* 269:1885–1888, 1995.

Campbell, *MONOCLONAL ANTIBODY TECHNOLOGY LABORATORY TECHNIQUES IN BIOCHEMISTRY AND MOLECULAR BIOLOGY,* Vol. 13, Burden and Von Knippenberg, eds. pp. 75–83, Elsevier, Amsterdam, 1984.

Cavener & Ray, *Nuc. Acids Res.,* 19:3185–3192, 1991.

Chen and Okayama, *Mol. Cell Biol.,* 7:2745–2752, 1987.

Cheng et al., *Science,* 267:1494–1498, 1995.

Chiou et al., *J. Virology,* 68:6553–6566, 1994.

Chou and Fasman, *Biochemistry* 13(2):222–245, 1974a.

Chou and Fasman, *Biochemistry* 13(2):211–222, 1974b.

Chou and Fasman, *Adv. Enzymol. Relat. Areas Mol. Biol.* 47:45–148, 1978a.

Chou and Fasman, *Ann. Rev. Biochem.* 47:251–276, 1978b.

Chou and Fasman, *Biophys. J.* 26:367–384, 1979.

Clem et al., *Science,* 254:1388–1390, 1991.

Clem & Miller, *J. Virology,* 67:3730–3738, 1993.

Clem & Miller, In Apoptosis II: The Molecular Basis of Apoptosis in Disease, L. D. Tomei and F. O. Cope, eds. (Cold Spring Harbor Laboratory Press), pp. 89–110, 1994a.

Clem & Miller, *Mol. Cell. Biol.,* 14:5212–5222, 1994b.

Coakley and James, *Anal. Biochem.* 85:90–97, 1978.

Coffin, In: *Virology,* Fields et al. (eds.), New York: Raven Press, pp. 1437–1500, 1990.

Cole et al., In: *Mechanisms of Injury,* eds. Meyn, R. E. & Withers, H. R., 1980.

Couch et al., *Am. Rev. Resp. Dis.,* 88:394–403, 1963.

Coupar et al., *Gene,* 68:1–10, 1988.

Crook et al., *J. Virology,* 67:2168–2174, 1993.

de The et al., *Cell,* 66:675–684, 1991.

Debbas & White, *Genes and Dev.,* 7:546–554, 1993.

Dubensky et al,. *Proc. Nat. Acad. Sci. USA,* 81:7529–7533, 1984.

Duckett et al., *Mol. Cell. Biol.,* 13:1315–1322, 1993.

Farrow et al., *Nature,* 374:731–733 (1995).

Fechheimer et al., *Proc. Nat'l Acad. Sci. USA,* 84:8463–8467, 1987.

Ferkol et al., *FASEB J.,* 7:1081–1091, 1993.

Fernandes-Alnemri et al., *Cancer Res.,* 55:2737–2742, 1995.

Fetrow & Bryant, *Biotechnology* 11:479–483, 1993.

Fraley et al., *Proc. Nat'l Acad. Sci USA,* 76:3348–3352, 1979.

Freshner, "Animal Cell Culture: A Practical Approach," Second Edition, Oxford/New York, IRL Press, Oxford University Press, 1992.

Friedmann, *Science,* 244:1275–1281, 1989.

Friesen & Miller, *J. Virology,* 61:2264–2272, 1987.

Gagliardini et al, *Science,* 263:826–828, 1994.

Gefter et al., *Somatic Cell Genet.* 3:231–236, 1977.

Ghosh-Choudhury, et al., *EMBO J.,* 1733–1739, 1987.

Ghosh and Bachhawat, In: Wu G. and C. Wu ed. Liver diseases, targeted diagnosis and therapy using specific receptors and ligands. New York: Marcel Dekker, pp. 87–104, 1991.

Goding, *MONOCLONAL ANTIBODIES: PRINCIPLES AND PRACTICE,* 2d ed., Academic Press, Orlando, Fla., pp. 60–61, 65–66, 71–74 (1986).

Gomez-Foix et al., *J. Biol. Chem.,* 267:25129–25134, 1992.

Gopal, *Mol. Cell Biol.,* 5:1188–1190, 1985.

Gorman et al., *Mol. Cell. Biol.,* 2:1044–1051, 1982.

Graham, et al., *J. Gen Virol.* 36:59–72, 1977.

Graham and Prevec, In: E. J. Murray (ed.), *Methods in Molecular Biology, Gene Transfer and Expression Protocols,* New Jersey: The Humana Press Inc., 109–128, 1991.

Graham and Van Der Eb, *Virology,* 52:456–467, 1973.

Grunhaus & Horwitz, *Semin. Virology,* 3:237–2542, 1992.

Harland and Weintraub, *J. Cell Biol.,* 101:1094–1099, 1985.

Henderson et al., *Proc. Natl. Acad. Sci. USA,* 90:8479–8483, 1993.

Hermonat and Muzycska, *Proc. Nat'l Acad. Sci. USA,* 81:6466–6470, 1984.

Hersdorffer et al., *DNA Cell Biol.,* 9:713–723, 1990.

Hershberger et al., *J. Virology,* 66:5525–5533, 1992.

Hershberger et al., *J. Virology,* 68:3467–3477, 1994.

Hertz & Huang, *J. Virology,* 66:857–864, 1992.

Herz and Gerard, *Proc. Nat'l Acad. Sci. USA* 90:2812–2816, 1993.

Herz and Roizman, *Cell* 33:145–151, 1983.

Horwich et al., *J. Virol.,* 64:642–650, 1990.

Hsiao, *Nucleic Acid Res.,* 19:2787, 1991.

Hu et al., *J. Biol. Chem.,* 269:30069–30072, 1994.

Jameson and Wolf, *Comput. Appl. Biosci.* 4(1):181–186, 1988.

Johnson et al., *BIOTECHNOLOGY AND PHARMACY,* Pezzuto et al., eds., Chapman and Hall, New York, 1993.

Jones and Shenk, *Cell,* 13:181–188, 1978.

June et al., *Mol. Cell. Biol.,* 7:4472–4481, 1987.

Kamita et al., *J. Virology,* 67:455–463, 1993.

Kaneda et al., *Science,* 243:375–378, 1989.

Karlsson et. al., *EMBO J.,* 5:2377–2385, 1986.

Kato et al., *J. Biol. Chem.,* 266:3361–3364, 1991.

Klein et al., *Nature,* 327:70–73, 1987.

Kohler and Milstein, *Nature* 256:495–497, 1975.

Kohler and Milstein, *Eur. J. Immunol.* 6:511–519, 1976.

Komiyama et al., *J. Biol. Chem.,* 269:19331–19337, 1994.

Kumar et al., *Genes and Dev.,* 8:1613–1626, 1994.

Kyte and Doolittle, *J. Mol. Biol.* 157(1):105–132, 1982.

Laemmli et. al., *Nature,* 227:680, 1970.

Le Gal La Salle et al., *Science* 259:988–990, 1993.

Levine et al., *Nature,* 361:739–742, 1993.

Levrero et al., *Gene,* 101:195–202, 1991.

Los et al., *Nature,* 375:81–83, 1995.

Lovering et al., *Proc. Natl. Acad. Sci. USA,* 90:2112–2116, 1993.

Lowry et al., *J. Biol. Chem.* 193:265–275, 1951.

Lustig et al., *J. Virology,* 62:2329–2336, 1988.

Mann et al., *Cell,* 33:153–159, 1983.

Markowitz et al., *J. Virol.,* 62:1120–1124, 1988.

Miura et al., *Cell,* 75:653–660, 1993.

Mizrahi, *Process Biochem., (August):*9–12, 1983.

Mulligan, *Science,* 260:926–932, 1993.

Nicolas and Rubenstein, In: *Vectors: A survey of molecular cloning vectors and their uses,* Rodriguez and Denhardt (eds.), Stoneham: Butterworth, pp. 494–513, 1988.

Nicolau and Sene, *Biochem. Biophys. Acta,* 721:185–190, 1982.

Nicolau et al., *Methods Enzymol.,* 149:157–176, 1987.

Oltvai & Korsmeyer, *Cell,* 79:189–192, 1994.

Paskind et al., *Virology,* 67:242–248, 1975.

Perales et al., *Proc. Natl. Acad. Sci. USA,* 91:4086–4090, 1994.

Perkins et al., *J. Virology,* 68:6820–6823, 1994.

Phillips et al., In: *Large Scale Mammalian Cell Culture* (Feder, J. and Tolbert, W. R., eds.), Academic Press, Orlando, Fla., U.S.A., 1985.

Potter et al., *Proc. Nat'l Acad. Sci. USA,* 81:7161–7165, 1984.

Rabizadeh et al., *J. Neurochem.,* 61:2318–2321, 1993.

Ragot et al., *Nature,* 361:647–650, 1993.

Renan, *Radiother. Oncol.,* 19:197–218, 1990.

Rich et al., *Hum. Gene Ther.,* 4:461–476, 1993.

Ridgeway, In: Rodriguez R L, Denhardt D T, ed. Vectors: A survey of molecular cloning vectors and their uses. Stoneham: Butterworth, pp.467–492, 1988.

Rippe et al., *Mol. Cell Biol.,* 10:689–695, 1990.

Rosenfeld et al., *Science,* 252:431–434, 1991.

Rosenfeld et al., *Cell,* 68:143–155,1992.

Ross et al., *Gene,* 139:219–221, 1994.

Rothe et al., *Cell,* 78.681–692, 1994.

Roux et al., *Proc. Natl. Acad. Sci USA,* 86:9079–9083, 1989.

Roy et al., *Cell,* 80:167–178, 1995.

Sabbatini et al., *Mol. Cell. Biol.,* 15:1060–1070, 1995.

Sato et al., *FEBS Lett.,* 358:113–118, 1995.

Song & Donner, *Biochem. J.,* 309:825–829, 1995.

Stratford-Perricaudet and Perricaudet, pp. 51–61, In: *Human Gene Transfer,* Eds, O. Cohen-Haguenauer and M. Boiron, Editions John Libbey Eurotext, France, 1991.

Stratford-Perricaudet et al., *Hum. Gene Ther.,* 1:241–256, 1990.

Temin, In: *Gene Transfer,* Kucherlapati (ed.), New York: Plenum Press, pp. 149–188, 1986.

Tewari and Dixit, *J. Biol. Chem.* 270:3255–3260, 1995.

Tewari et al., *Cell,* 81:1–20, 1995.

Thornberry et al., *Nature,* 356:768–774, 1992.

Top et al., *J. Infect. Dis.,* 124:155–160, 1971.

Tur-Kaspa et al., *Mol. Cell Biol.,* 6:716–718, 1986.

Vaux et al., *Cell,* 76:777–779, 1994.

Wagner et al., *Science,* 260:1510–1513, 1990.

Wang et al., *Cell,* 78:739–750, 1994.

Weinberger et al., *Science* 228:740–742, 1985.

White, E., *Genes and Dev.* 7:2277–2284, 1993.

White & Gooding, *The Molecular Basis of Apoptosis in Disease,* L. D. Tomei and F. O. Cope, eds. (Cold Spring Harbor Laboratory Press), pp. 111–141, 1994.

White et al., *Science,* 264:677–683, 1994.

Wolf et al., *Comput. Appl. Biosci.* 4(1):187–191, 1988.

Wong et al., *Gene,* 10:87–94, 1980.

Wu and Wu, *J. Biol. Chem,* 262:4429–4432, 1987.

Wu and Wu, *Biochemistry,* 27:887–892, 1988.

Wu and Wu, *Adv. Drug Delivery Rev.,* 12:159–167, 1993.

Xue & Horvitz, *Nature,* 377:248–251, 1995.

Yang et al., *Proc. Nat'l Acad. Sci. USA,* 87:9568–9572, 1990.

Yuan et al., *Cell,* 75:641–652, 1993.

Zelenin et al., *FEBS Lett.,* 280:94–96, 1991.

What is claimed is:

1. An isolated and purified polynucleotide encoding an inhibitor of apoptosis (iap)-like protein (ilp), where said ilp has the amino acid sequence of SEQ ID NO: 1 (FIG. 2B) or SEQ ID NO: 2 (FIG. 2C).

2. The polynucleotide of claim 1, wherein said ilp has the amino acid sequence of SEQ ID NO: 2 (FIG. 2C).

3. The polynucleotide of claim 1, wherein said ilp has the amino acid sequence of SEQ ID NO: 1 (FIG. 2B).

4. A recombinant host cell comprising a recombinant polynucleotide encoding an inhibitor of apoptosis (iap)-like protein (ilp), where said ilp has the amino acid sequence of SEQ ID NO: 1 (FIG. 2B) or SEQ ID NO: 2 (FIG. 2C).

5. A method for producing an inhibitor of apoptosis (iap)-like protein (ilp), where said ilp has the amino acid sequence of SEQ ID NO: 1 (FIG. 2B) or SEQ ID NO: 2 (FIG. 2C), comprising the steps of:

(a) providing a recombinant host cell comprising a recombinant polynucleotide encoding said ilp, and (b) culturing said recombinant host cell to produce said ilp.

6. The method of claim 5, further comprising the step of isolating said ilp.

* * * * *

SEQUENCE LISTING

```
(1) GENERAL INFORMATION:

   (iii) NUMBER OF SEQUENCES: 58


(2) INFORMATION FOR SEQ ID NO:1:

     (i) SEQUENCE CHARACTERISTICS:
          (A) LENGTH: 497 amino acids
          (B) TYPE: amino acid
          (C) STRANDEDNESS:
          (D) TOPOLOGY: linear

    (xi) SEQUENCE DESCRIPTION: SEQ ID NO:1:

Met Thr Glu Leu Gly Met Glu Leu Glu Ser Val Arg Leu Ala Thr Phe
1               5                   10                  15

Gly Glu Trp Pro Leu Asn Ala Pro Val Ser Ala Glu Asp Leu Val Ala
            20                  25                  30

Asn Gly Phe Phe Ala Thr Gly Asn Trp Leu Glu Ala Glu Cys His Phe
        35                  40                  45

Cys His Val Arg Ile Asp Arg Trp Glu Tyr Gly Asp Gln Val Ala Ala
    50                  55                  60

Gly His Arg Arg Ser Ser Pro Ile Cys Ser Met Val Leu Ala Pro Asn
65                  70                  75                  80

His Cys Gly Asn Val Pro Arg Ser Gln Glu Ser Asp Asn Glu Gly Asn
                85                  90                  95

Ser Val Val Asp Ser Pro Glu Ser Cys Ser Cys Pro Asp Leu Leu Leu
            100                 105                 110

Glu Ala Asn Arg Leu Val Thr Phe Lys Asp Trp Pro Asn Pro Asn Ile
        115                 120                 125

Thr Pro Gln Ala Leu Ala Lys Ala Gly Phe Tyr Tyr Leu Asn Arg Leu
    130                 135                 140

Asp His Val Lys Cys Val Trp Cys Asn Gly Val Ile Ala Lys Trp Glu
145                 150                 155                 160

Lys Asn Asp Asn Ala Phe Glu Glu His Lys Arg Phe Phe Pro Gln Cys
                165                 170                 175

Pro Arg Val Gln Met Gly Pro Leu Ile Glu Phe Ala Thr Gly Lys Asn
            180                 185                 190

Leu Asp Glu Leu Gly Ile Gln Pro Thr Thr Leu Pro Leu Arg Pro Lys
        195                 200                 205

Tyr Ala Cys Val Asp Ala Arg Leu Arg Thr Phe Thr Asp Trp Pro Ile
    210                 215                 220

Ser Asn Ile Gln Pro Ala Ser Ala Leu Ala Gln Ala Gly Leu Tyr Tyr
225                 230                 235                 240

Gln Lys Ile Gly Asp Gln Val Arg Cys Phe His Cys Asn Ile Gly Leu
                245                 250                 255

Arg Ser Trp Gln Lys Glu Asp Glu Pro Trp Phe Glu His Ala Lys Trp
            260                 265                 270

Ser Pro Lys Cys Gln Phe Val Leu Leu Ala Lys Gly Pro Ser Tyr Val
        275                 280                 285

Ser Glu Val Leu Ala Thr Thr Ala Ala Asn Ala Ser Ser Pro Pro Ala
    290                 295                 300

Thr Ala Pro Ala Pro Thr Leu Gln Ala Asp Val Leu Met Asp Glu Ala
305                 310                 315                 320

Pro Ala Lys Glu Ala Leu Ala Leu Gly Ile Asp Gly Gly Val Val Arg
```

-continued

```
                325                 330                 335

Asn Ala Ile Gln Arg Lys Leu Leu Ser Ser Gly Cys Ala Phe Ser Thr
            340                 345                 350

Leu Asp Glu Leu Leu His Asp Ile Phe Asp Asp Ala Gly Ala Gly Ala
        355                 360                 365

Asp Trp Arg Cys Ala Ser Arg Glu Pro Ser Ala Pro Phe Ile Glu Pro
    370                 375                 380

Cys Gln Ala Thr Thr Ser Lys Ala Ala Ser Val Pro Ile Pro Val Ala
385                 390                 395                 400

Asp Ser Ile Pro Ala Lys Pro Gln Ala Ala Glu Ala Val Ala Asn Ile
                405                 410                 415

Ser Lys Ile Thr Asp Glu Ile Gln Lys Met Ser Val Ala Thr Pro Asn
            420                 425                 430

Gly Asn Leu Ser Leu Glu Glu Glu Asn Arg Gln Leu Lys Asp Ala Arg
        435                 440                 445

Leu Cys Lys Val Cys Leu Asp Glu Glu Val Gly Val Val Phe Leu Pro
    450                 455                 460

Cys Gly His Leu Ala Thr Cys Asn Gln Cys Ala Pro Ser Val Ala Asn
465                 470                 475                 480

Cys Pro Met Cys Arg Ala Asp Ile Lys Gly Phe Val Arg Thr Phe Leu
                485                 490                 495

Ser
```

(2) INFORMATION FOR SEQ ID NO:2:

(i) SEQUENCE CHARACTERISTICS:
(A) LENGTH: 497 amino acids
(B) TYPE: amino acid
(C) STRANDEDNESS:
(D) TOPOLOGY: linear (xi) SEQUENCE DESCRIPTION: SEQ ID NO:2:

```
Met Thr Phe Asn Ser Phe Glu Gly Ser Lys Thr Cys Val Pro Ala Asp
1               5                   10                  15

Ile Asn Lys Glu Glu Glu Phe Val Glu Glu Phe Asn Arg Leu Lys Thr
            20                  25                  30

Phe Ala Asn Phe Pro Ser Gly Ser Pro Val Ser Ala Ser Thr Leu Ala
        35                  40                  45

Arg Ala Gly Phe Leu Tyr Thr Gly Glu Gly Asp Thr Val Arg Cys Phe
    50                  55                  60

Ser Cys His Ala Ala Val Asp Arg Trp Gln Tyr Gly Asp Ser Ala Val
65                  70                  75                  80

Gly Arg His Arg Lys Val Ser Pro Asn Cys Arg Phe Ile Asn Gly Phe
                85                  90                  95

Tyr Leu Glu Asn Ser Ala Thr Gln Ser Thr Asn Ser Gly Ile Gln Asn
            100                 105                 110

Gly Gln Tyr Lys Val Glu Asn Tyr Leu Gly Ser Arg Asp His Phe Ala
        115                 120                 125

Leu Asp Arg Pro Ser Glu Thr His Ala Asp Tyr Leu Leu Arg Thr Gly
    130                 135                 140

Gln Val Val Asp Ile Ser Asp Thr Ile Tyr Pro Arg Asn Pro Ala Met
145                 150                 155                 160

Tyr Ser Glu Glu Ala Arg Leu Lys Ser Phe Gln Asn Trp Pro Asp Tyr
                165                 170                 175

Ala His Leu Thr Pro Arg Glu Leu Ala Ser Ala Gly Leu Tyr Tyr Thr
```

-continued

```
            180                 185                 190

Gly Ile Gly Asp Gln Val Gln Cys Phe Cys Cys Gly Gly Lys Leu Lys
        195                 200                 205

Asn Trp Glu Pro Cys Asp Arg Ala Trp Ser Glu His Arg Arg His Phe
    210                 215                 220

Pro Asn Cys Phe Phe Val Leu Gly Arg Asn Leu Asn Ile Arg Ser Glu
225                 230                 235                 240

Ser Asp Ala Val Ser Ser Asp Arg Asn Phe Pro Asn Ser Thr Asn Leu
                245                 250                 255

Pro Arg Asn Pro Ser Met Ala Asp Tyr Glu Ala Arg Ile Phe Thr Phe
            260                 265                 270

Gly Thr Trp Ile Tyr Ser Val Asn Lys Glu Gln Leu Ala Arg Ala Gly
        275                 280                 285

Phe Tyr Ala Leu Gly Glu Gly Asp Lys Val Lys Cys Phe His Cys Gly
    290                 295                 300

Gly Gly Leu Thr Asp Trp Lys Pro Ser Glu Asp Pro Trp Glu Gln His
305                 310                 315                 320

Ala Lys Trp Tyr Pro Gly Cys Lys Tyr Leu Leu Glu Gln Lys Gly Gln
                325                 330                 335

Glu Tyr Ile Asn Asn Ile His Leu Thr His Ser Leu Glu Glu Cys Leu
            340                 345                 350

Val Arg Thr Thr Glu Lys Thr Pro Ser Leu Thr Arg Arg Ile Asp Asp
        355                 360                 365

Thr Ile Phe Gln Asn Pro Met Val Gln Glu Ala Ile Arg Met Gly Phe
    370                 375                 380

Ser Phe Lys Asp Ile Lys Lys Ile Met Glu Glu Lys Ile Gln Ile Ser
385                 390                 395                 400

Gly Ser Asn Tyr Lys Ser Leu Glu Val Leu Val Ala Asp Leu Val Asn
                405                 410                 415

Ala Gln Lys Asp Ser Met Pro Asp Glu Ser Ser Gln Thr Ser Leu Gln
            420                 425                 430

Lys Glu Ile Ser Thr Glu Glu Gln Leu Arg Arg Leu Gln Glu Glu Lys
        435                 440                 445

Leu Cys Lys Ile Cys Met Asp Arg Asn Ile Ala Ile Val Phe Val Pro
    450                 455                 460

Cys Gly His Leu Val Thr Cys Lys Gln Cys Ala Glu Ala Val Asp Lys
465                 470                 475                 480

Cys Pro Met Cys Tyr Thr Val Ile Thr Phe Lys Gln Lys Ile Phe Met
                485                 490                 495

Ser
```

(2) INFORMATION FOR SEQ ID NO:3:

(i) SEQUENCE CHARACTERISTICS:
(A) LENGTH: 14 amino acids
(B) TYPE: amino acid
(C) STRANDEDNESS:
(D) TOPOLOGY: linear (xi) SEQUENCE DESCRIPTION: SEQ ID NO:3:

```
Lys Asn Lys Ala Ala Arg Leu Gly Thr Tyr Thr Asn Trp Pro
1               5                   10
```

(2) INFORMATION FOR SEQ ID NO:4:

(i) SEQUENCE CHARACTERISTICS:

(A) LENGTH: 59 amino acids
(B) TYPE: amino acid
(C) STRANDEDNESS:
(D) TOPOLOGY: linear (xi) SEQUENCE DESCRIPTION: SEQ ID NO:4:

```
Val Gln Phe Leu Glu Pro Ser Arg Met Ala Ala Ser Gly Phe Tyr Tyr
1               5                   10                  15

Leu Gly Arg Gly Asp Glu Val Arg Cys Ala Phe Cys Lys Val Glu Ile
            20                  25                  30

Thr Asn Trp Val Arg Gly Asp Asp Pro Glu Thr Asp His Lys Arg Trp
        35                  40                  45

Ala Pro Gln Cys Pro Phe Val Arg Asn Asn Ala
    50                  55
```

(2) INFORMATION FOR SEQ ID NO:5:

(i) SEQUENCE CHARACTERISTICS:
(A) LENGTH: 14 amino acids
(B) TYPE: amino acid
(C) STRANDEDNESS:
(D) TOPOLOGY: linear (xi) SEQUENCE DESCRIPTION: SEQ ID NO:5:

```
Ala Thr Glu Ala Ala Arg Leu Arg Thr Phe Ala Glu Trp Pro
1               5                   10
```

(2) INFORMATION FOR SEQ ID NO:6:

(i) SEQUENCE CHARACTERISTICS:
(A) LENGTH: 60 amino acids
(B) TYPE: amino acid
(C) STRANDEDNESS:
(D) TOPOLOGY: linear (xi) SEQUENCE DESCRIPTION: SEQ ID NO:6:

```
Arg Gly Leu Lys Gln Arg Pro Glu Glu Leu Ala Glu Ala Gly Phe Phe
1               5                   10                  15

Tyr Thr Gly Gln Gly Asp Lys Thr Arg Cys Phe Cys Cys Asp Gly Gly
            20                  25                  30

Leu Lys Asp Trp Glu Pro Asp Asp Ala Pro Trp Gln Gln His Ala Arg
        35                  40                  45

Trp Tyr Asp Arg Cys Glu Tyr Val Leu Leu Val Lys
    50                  55                  60
```

(2) INFORMATION FOR SEQ ID NO:7:

(i) SEQUENCE CHARACTERISTICS:
(A) LENGTH: 15 amino acids
(B) TYPE: amino acid
(C) STRANDEDNESS:
(D) TOPOLOGY: linear (xi) SEQUENCE DESCRIPTION: SEQ ID NO:7:

```
Glu Leu Glu Ser Val Arg Leu Ala Thr Phe Gly Glu Trp Pro Leu
1               5                   10                  15
```

(2) INFORMATION FOR SEQ ID NO:8:

(i) SEQUENCE CHARACTERISTICS:
(A) LENGTH: 59 amino acids
(B) TYPE: amino acid
(C) STRANDEDNESS:
(D) TOPOLOGY: linear -continued (xi) SEQUENCE DESCRIPTION: SEQ ID NO:8:

```
Asn Ala Pro Val Ser Ala Glu Asp Leu Val Ala Asn Gly Phe Phe Ala
1               5                   10                  15

Thr Gly Asn Trp Leu Glu Ala Glu Cys His Phe Cys His Val Arg Ile
            20                  25                  30

Asp Arg Trp Glu Tyr Gly Asp Gln Val Ala Ala Gly His Arg Arg Ser
        35                  40                  45

Ser Pro Ile Cys Ser Met Val Leu Ala Pro Asn
    50                  55
```

(2) INFORMATION FOR SEQ ID NO:9:

(i) SEQUENCE CHARACTERISTICS:
(A) LENGTH: 14 amino acids
(B) TYPE: amino acid
(C) STRANDEDNESS:
(D) TOPOLOGY: linear (xi) SEQUENCE DESCRIPTION: SEQ ID NO:9:

```
Leu Leu Glu Ala Asn Arg Leu Val Thr Phe Lys Asp Trp Pro
1               5                   10
```

(2) INFORMATION FOR SEQ ID NO:10:

(i) SEQUENCE CHARACTERISTICS:
(A) LENGTH: 59 amino acids
(B) TYPE: amino acid
(C) STRANDEDNESS:
(D) TOPOLOGY: linear (xi) SEQUENCE DESCRIPTION: SEQ ID NO:10:

```
Asn Pro Asn Ile Thr Pro Gln Ala Leu Ala Lys Ala Gly Phe Tyr Tyr
1               5                   10                  15

Leu Asn Arg Leu Asp His Val Lys Cys Val Trp Cys Asn Gly Val Ile
            20                  25                  30

Ala Lys Trp Glu Lys Asn Asp Asn Ala Phe Glu Glu His Lys Arg Phe
        35                  40                  45

Phe Pro Gln Cys Pro Arg Val Gln Met Gly Pro
    50                  55
```

(2) INFORMATION FOR SEQ ID NO:11:

(i) SEQUENCE CHARACTERISTICS:
(A) LENGTH: 14 amino acids
(B) TYPE: amino acid
(C) STRANDEDNESS:
(D) TOPOLOGY: linear (xi) SEQUENCE DESCRIPTION: SEQ ID NO:11:

```
Ala Cys Val Asp Ala Arg Leu Arg Thr Phe Thr Asp Trp Pro
1               5                   10
```

(2) INFORMATION FOR SEQ ID NO:12:

(i) SEQUENCE CHARACTERISTICS:
(A) LENGTH: 60 amino acids
(B) TYPE: amino acid
(C) STRANDEDNESS:
(D) TOPOLOGY: linear (xi) SEQUENCE DESCRIPTION: SEQ ID NO:12:

```
Ile Ser Asn Ile Gln Pro Ala Ser Ala Leu Ala Gln Ala Gly Leu Tyr
1               5                   10                  15
```

-continued

```
Tyr Gln Lys Ile Gly Asp Gln Val Arg Cys Phe His Cys Asn Ile Gly
            20                  25                  30

Leu Arg Ser Trp Gln Lys Glu Asp Glu Pro Trp Phe Glu His Ala Lys
        35                  40                  45

Trp Ser Pro Lys Cys Gln Phe Val Leu Leu Ala Lys
    50                  55                  60
```

(2) INFORMATION FOR SEQ ID NO:13:

(i) SEQUENCE CHARACTERISTICS:
(A) LENGTH: 15 amino acids
(B) TYPE: amino acid
(C) STRANDEDNESS:
(D) TOPOLOGY: linear (xi) SEQUENCE DESCRIPTION: SEQ ID NO:13:

```
Val Glu Glu Phe Asn Arg Leu Lys Thr Phe Ala Asn Phe Pro Ser
1               5                   10                  15
```

(2) INFORMATION FOR SEQ ID NO:14:

(i) SEQUENCE CHARACTERISTICS:
(A) LENGTH: 59 amino acids
(B) TYPE: amino acid
(C) STRANDEDNESS:
(D) TOPOLOGY: linear (xi) SEQUENCE DESCRIPTION: SEQ ID NO:14:

```
Gly Ser Pro Val Ser Ala Ser Thr Leu Ala Arg Ala Gly Phe Leu Tyr
1               5                   10                  15

Thr Gly Glu Gly Asp Thr Val Arg Cys Phe Ser Cys His Ala Ala Val
            20                  25                  30

Asp Arg Trp Gln Tyr Gly Asp Ser Ala Val Gly Arg His Arg Lys Val
        35                  40                  45

Ser Pro Asn Cys Arg Phe Ile Asn Gly Phe Tyr
    50                  55
```

(2) INFORMATION FOR SEQ ID NO:15:

(i) SEQUENCE CHARACTERISTICS:
(A) LENGTH: 18 amino acids
(B) TYPE: amino acid
(C) STRANDEDNESS:
(D) TOPOLOGY: linear (xi) SEQUENCE DESCRIPTION: SEQ ID NO:15:

```
Tyr Ser Glu Glu Ala Arg Leu Lys Ser Phe Gln Asn Trp Pro Asp Tyr
1               5                   10                  15

Ala His
```

(2) INFORMATION FOR SEQ ID NO:16:

(i) SEQUENCE CHARACTERISTICS:
(A) LENGTH: 56 amino acids
(B) TYPE: amino acid
(C) STRANDEDNESS:
(D) TOPOLOGY: linear (xi) SEQUENCE DESCRIPTION: SEQ ID NO:16:

```
Leu Thr Pro Arg Glu Leu Ala Ser Ala Gly Leu Tyr Tyr Thr Gly Ile
1               5                   10                  15

Gly Asp Gln Val Gln Cys Phe Cys Cys Gly Gly Lys Leu Lys Asn Trp
            20                  25                  30
```

-continued

```
Glu Pro Cys Asp Arg Ala Trp Ser Glu His Arg Arg His Phe Pro Asn
        35                  40                  45

Cys Phe Phe Val Leu Gly Arg Asn
    50                  55
```

(2) INFORMATION FOR SEQ ID NO:17:

(i) SEQUENCE CHARACTERISTICS:
(A) LENGTH: 14 amino acids
(B) TYPE: amino acid
(C) STRANDEDNESS:
(D) TOPOLOGY: linear (xi) SEQUENCE DESCRIPTION: SEQ ID NO:17:

```
Ala Asp Tyr Glu Ala Arg Ile Phe Thr Phe Gly Thr Trp Ile
1               5                   10
```

(2) INFORMATION FOR SEQ ID NO:18:

(i) SEQUENCE CHARACTERISTICS:
(A) LENGTH: 5 amino acids
(B) TYPE: amino acid
(C) STRANDEDNESS:
(D) TOPOLOGY: linear (xi) SEQUENCE DESCRIPTION: SEQ ID NO:18:

```
Tyr Ser Val Asn Lys
1               5
```

(2) INFORMATION FOR SEQ ID NO:19:

(i) SEQUENCE CHARACTERISTICS:
(A) LENGTH: 53 amino acids
(B) TYPE: amino acid
(C) STRANDEDNESS:
(D) TOPOLOGY: linear (xi) SEQUENCE DESCRIPTION: SEQ ID NO:19:

```
Glu Gln Leu Ala Arg Ala Gly Phe Tyr Ala Leu Gly Glu Gly Asp Lys
1               5                   10                  15

Val Lys Cys Phe His Cys Gly Gly Gly Leu Thr Asp Trp Lys Pro Ser
            20                  25                  30

Glu Asp Pro Trp Glu Gln His Ala Lys Trp Tyr Pro Gly Cys Lys Tyr
        35                  40                  45

Leu Leu Glu Gln Lys
    50
```

(2) INFORMATION FOR SEQ ID NO:20:

(i) SEQUENCE CHARACTERISTICS:
(A) LENGTH: 20 amino acids
(B) TYPE: amino acid
(C) STRANDEDNESS:
(D) TOPOLOGY: linear (xi) SEQUENCE DESCRIPTION: SEQ ID NO:20:

```
Arg Ser Glu Ala Lys Arg Leu Lys Thr Phe Val Thr Tyr Glu Pro Tyr
1               5                   10                  15

Ser Ser Trp Ile
            20
```

(2) INFORMATION FOR SEQ ID NO:21:

(i) SEQUENCE CHARACTERISTICS:
(A) LENGTH: 54 amino acids (B) TYPE: amino acid
(C) STRANDEDNESS:
(D) TOPOLOGY: linear (xi) SEQUENCE DESCRIPTION: SEQ ID NO:21:

```
Pro Gln Glu Met Ala Ala Ala Gly Phe Tyr Phe Thr Gly Val Lys Ser
1               5                   10                  15

Gly Ile Gln Cys Phe Cys Cys Ser Leu Ile Leu Phe Gly Ala Gly Leu
            20                  25                  30

Thr Arg Leu Pro Ile Glu Asp His Lys Arg Phe His Pro Asp Cys Gly
        35                  40                  45

Phe Leu Leu Asn Lys Asp
    50
```

(2) INFORMATION FOR SEQ ID NO:22:

(i) SEQUENCE CHARACTERISTICS:
(A) LENGTH: 75 amino acids
(B) TYPE: amino acid
(C) STRANDEDNESS:
(D) TOPOLOGY: linear (xi) SEQUENCE DESCRIPTION: SEQ ID NO:22:

```
Gln Glu Glu Glu Ala Arg Leu Ala Ser Phe Arg Asn Trp Pro Phe Tyr
1               5                   10                  15

Val Gln Gly Ile Ser Pro Cys Val Leu Ser Glu Ala Gly Phe Val Phe
            20                  25                  30

Thr Gly Lys Gln Asp Thr Val Gln Cys Phe Ser Cys Gly Gly Cys Leu
        35                  40                  45

Gly Asn Trp Glu Glu Gly Asp Asp Pro Trp Lys Glu His Ala Lys Trp
    50                  55                  60

Phe Pro Lys Cys Glu Phe Leu Arg Ser Lys Lys
65                  70                  75
```

(2) INFORMATION FOR SEQ ID NO:23:

(i) SEQUENCE CHARACTERISTICS:
(A) LENGTH: 18 amino acids
(B) TYPE: amino acid
(C) STRANDEDNESS:
(D) TOPOLOGY: linear (xi) SEQUENCE DESCRIPTION: SEQ ID NO:23:

```
Ala Tyr Glu Glu Leu Arg Leu Asp Ser Phe Lys Asp Trp Pro Arg Glu
1               5                   10                  15

Ser Ala
```

(2) INFORMATION FOR SEQ ID NO:24:

(i) SEQUENCE CHARACTERISTICS:
(A) LENGTH: 56 amino acids
(B) TYPE: amino acid
(C) STRANDEDNESS:
(D) TOPOLOGY: linear (xi) SEQUENCE DESCRIPTION: SEQ ID NO:24:

```
Val Gly Val Ala Ala Leu Ala Lys Ala Gly Leu Phe Tyr Thr Gly Ile
1               5                   10                  15

Lys Asp Ile Val Gln Cys Phe Ser Cys Gly Gly Cys Leu Glu Lys Trp
            20                  25                  30

Gln Glu Gly Asp Asp Pro Leu Asp Asp His Thr Arg Cys Phe Pro Asn
        35                  40                  45
```

-continued

```
Cys Pro Phe Leu Gln Asn Met Lys
    50                  55


(2) INFORMATION FOR SEQ ID NO:25:

     (i) SEQUENCE CHARACTERISTICS:
          (A) LENGTH: 7 amino acids
          (B) TYPE: amino acid
          (C) STRANDEDNESS:
          (D) TOPOLOGY: linear

    (xi) SEQUENCE DESCRIPTION: SEQ ID NO:25:

Ala Gly Phe Tyr Tyr Thr Gly
1               5


(2) INFORMATION FOR SEQ ID NO:26:

     (i) SEQUENCE CHARACTERISTICS:
          (A) LENGTH: 17 amino acids
          (B) TYPE: amino acid
          (C) STRANDEDNESS:
          (D) TOPOLOGY: linear

    (xi) SEQUENCE DESCRIPTION: SEQ ID NO:26:

Asp Arg Leu Cys Lys Ile Cys Leu Gly Ala Glu Lys Thr Val Cys Phe
1               5                   10                  15

Val


(2) INFORMATION FOR SEQ ID NO:27:

     (i) SEQUENCE CHARACTERISTICS:
          (A) LENGTH: 11 amino acids
          (B) TYPE: amino acid
          (C) STRANDEDNESS:
          (D) TOPOLOGY: linear

    (xi) SEQUENCE DESCRIPTION: SEQ ID NO:27:

Pro Cys Gly His Val Val Ala Cys Gly Lys Cys
1               5                   10


(2) INFORMATION FOR SEQ ID NO:28:

     (i) SEQUENCE CHARACTERISTICS:
          (A) LENGTH: 4 amino acids
          (B) TYPE: amino acid
          (C) STRANDEDNESS:
          (D) TOPOLOGY: linear

    (xi) SEQUENCE DESCRIPTION: SEQ ID NO:28:

Ala Gly Val Thr
1


(2) INFORMATION FOR SEQ ID NO:29:

     (i) SEQUENCE CHARACTERISTICS:
          (A) LENGTH: 8 amino acids
          (B) TYPE: amino acid
          (C) STRANDEDNESS:
          (D) TOPOLOGY: linear

    (xi) SEQUENCE DESCRIPTION: SEQ ID NO:29:

Thr Cys Pro Val Cys Arg Gly Gln
1               5


(2) INFORMATION FOR SEQ ID NO:30:
```

-continued

```
     (i) SEQUENCE CHARACTERISTICS:
          (A) LENGTH: 17 amino acids
          (B) TYPE: amino acid
          (C) STRANDEDNESS:
          (D) TOPOLOGY: linear

    (xi) SEQUENCE DESCRIPTION: SEQ ID NO:30:

Ala Arg Leu Cys Lys Val Cys Leu Asp Glu Glu Val Gly Val Val Phe
1               5                   10                  15

Leu


(2) INFORMATION FOR SEQ ID NO:31:

     (i) SEQUENCE CHARACTERISTICS:
          (A) LENGTH: 11 amino acids
          (B) TYPE: amino acid
          (C) STRANDEDNESS:
          (D) TOPOLOGY: linear

    (xi) SEQUENCE DESCRIPTION: SEQ ID NO:31:

Pro Cys Gly His Leu Ala Thr Cys Asn Gln Cys
1               5                   10


(2) INFORMATION FOR SEQ ID NO:32:

     (i) SEQUENCE CHARACTERISTICS:
          (A) LENGTH: 4 amino acids
          (B) TYPE: amino acid
          (C) STRANDEDNESS:
          (D) TOPOLOGY: linear

    (xi) SEQUENCE DESCRIPTION: SEQ ID NO:32:

Pro Ser Val Ala
1


(2) INFORMATION FOR SEQ ID NO:33:

     (i) SEQUENCE CHARACTERISTICS:
          (A) LENGTH: 8 amino acids
          (B) TYPE: amino acid
          (C) STRANDEDNESS:
          (D) TOPOLOGY: linear

    (xi) SEQUENCE DESCRIPTION: SEQ ID NO:33:

Asn Cys Pro Met Cys Arg Ala Asp
1               5


(2) INFORMATION FOR SEQ ID NO:34:

     (i) SEQUENCE CHARACTERISTICS:
          (A) LENGTH: 17 amino acids
          (B) TYPE: amino acid
          (C) STRANDEDNESS:
          (D) TOPOLOGY: linear

    (xi) SEQUENCE DESCRIPTION: SEQ ID NO:34:

Glu Lys Leu Cys Lys Ile Cys Met Asp Arg Asn Ile Ala Ile Val Phe
1               5                   10                  15

Val


(2) INFORMATION FOR SEQ ID NO:35:

     (i) SEQUENCE CHARACTERISTICS:
          (A) LENGTH: 11 amino acids
          (B) TYPE: amino acid
          (C) STRANDEDNESS:
          (D) TOPOLOGY: linear
```

(xi) SEQUENCE DESCRIPTION: SEQ ID NO:35:

Pro Cys Gly His Leu Val Thr Cys Lys Gln Cys
1 5 10

(2) INFORMATION FOR SEQ ID NO:36:

(i) SEQUENCE CHARACTERISTICS:
(A) LENGTH: 4 amino acids
(B) TYPE: amino acid
(C) STRANDEDNESS:
(D) TOPOLOGY: linear (xi) SEQUENCE DESCRIPTION: SEQ ID NO:36:

Glu Ala Val Asp
1

(2) INFORMATION FOR SEQ ID NO:37:

(i) SEQUENCE CHARACTERISTICS:
(A) LENGTH: 8 amino acids
(B) TYPE: amino acid
(C) STRANDEDNESS:
(D) TOPOLOGY: linear (xi) SEQUENCE DESCRIPTION: SEQ ID NO:37:

Lys Cys Pro Met Cys Tyr Thr Val
1 5

(2) INFORMATION FOR SEQ ID NO:38:

(i) SEQUENCE CHARACTERISTICS:
(A) LENGTH: 17 amino acids
(B) TYPE: amino acid
(C) STRANDEDNESS:
(D) TOPOLOGY: linear (xi) SEQUENCE DESCRIPTION: SEQ ID NO:38:

Lys Tyr Leu Cys Ser Ala Cys Lys Asn Ile Leu Arg Arg Pro Phe Gln
1 5 10 15

Ala (2) INFORMATION FOR SEQ ID NO:39:

(i) SEQUENCE CHARACTERISTICS:
(A) LENGTH: 6 amino acids
(B) TYPE: amino acid
(C) STRANDEDNESS:
(D) TOPOLOGY: linear (xi) SEQUENCE DESCRIPTION: SEQ ID NO:39:

Gln Cys Gly His Arg Tyr
1 5

(2) INFORMATION FOR SEQ ID NO:40:

(i) SEQUENCE CHARACTERISTICS:
(A) LENGTH: 22 amino acids
(B) TYPE: amino acid
(C) STRANDEDNESS:
(D) TOPOLOGY: linear (xi) SEQUENCE DESCRIPTION: SEQ ID NO:40:

Cys Ser Phe Cys Leu Thr Ser Ile Leu Ser Ser Gly Pro Gln Asn Cys
1 5 10 15

Ala Ala Cys Val Tyr Glu

```
            20


(2) INFORMATION FOR SEQ ID NO:41:

     (i) SEQUENCE CHARACTERISTICS:
          (A) LENGTH: 17 amino acids
          (B) TYPE: amino acid
          (C) STRANDEDNESS:
          (D) TOPOLOGY: linear

    (xi) SEQUENCE DESCRIPTION: SEQ ID NO:41:

Lys Tyr Lys Cys Glu Lys Cys His Leu Val Leu Cys Ser Pro Lys Gln
1               5                   10                  15

Thr


(2) INFORMATION FOR SEQ ID NO:42:

     (i) SEQUENCE CHARACTERISTICS:
          (A) LENGTH: 6 amino acids
          (B) TYPE: amino acid
          (C) STRANDEDNESS:
          (D) TOPOLOGY: linear

    (xi) SEQUENCE DESCRIPTION: SEQ ID NO:42:

Glu Cys Gly His Arg Phe
1               5


(2) INFORMATION FOR SEQ ID NO:43:

     (i) SEQUENCE CHARACTERISTICS:
          (A) LENGTH: 20 amino acids
          (B) TYPE: amino acid
          (C) STRANDEDNESS:
          (D) TOPOLOGY: linear

    (xi) SEQUENCE DESCRIPTION: SEQ ID NO:43:

Cys Glu Ser Cys Met Ala Ala Leu Leu Ser Ser Ser Ser Pro Lys Cys
1               5                   10                  15

Thr Ala Cys Gln
            20


(2) INFORMATION FOR SEQ ID NO:44:

     (i) SEQUENCE CHARACTERISTICS:
          (A) LENGTH: 17 amino acids
          (B) TYPE: amino acid
          (C) STRANDEDNESS:
          (D) TOPOLOGY: linear

    (xi) SEQUENCE DESCRIPTION: SEQ ID NO:44:

Phe Gln Leu Cys Lys Ile Cys Ala Glu Asn Asp Lys Asp Val Lys Ile
1               5                   10                  15

Glu


(2) INFORMATION FOR SEQ ID NO:45:

     (i) SEQUENCE CHARACTERISTICS:
          (A) LENGTH: 6 amino acids
          (B) TYPE: amino acid
          (C) STRANDEDNESS:
          (D) TOPOLOGY: linear

    (xi) SEQUENCE DESCRIPTION: SEQ ID NO:45:

Pro Cys Gly His Leu Met
1               5
```

-continued (2) INFORMATION FOR SEQ ID NO:46:

(i) SEQUENCE CHARACTERISTICS:
(A) LENGTH: 22 amino acids
(B) TYPE: amino acid
(C) STRANDEDNESS:
(D) TOPOLOGY: linear (xi) SEQUENCE DESCRIPTION: SEQ ID NO:46:

```
Cys Thr Ser Cys Leu Thr Ser Trp Gln Glu Ser Glu Gly Gln Gly Cys
1               5                   10                  15

Pro Phe Cys Arg Cys Glu
            20
```

(2) INFORMATION FOR SEQ ID NO:47:

(i) SEQUENCE CHARACTERISTICS:
(A) LENGTH: 24 amino acids
(B) TYPE: amino acid
(C) STRANDEDNESS:
(D) TOPOLOGY: linear (xi) SEQUENCE DESCRIPTION: SEQ ID NO:47:

```
Glu Leu Met Cys Pro Ile Cys Leu Asp Met Leu Lys Asn Thr Met Thr
1               5                   10                  15

Thr Lys Glu Cys Leu His Arg Phe
            20
```

(2) INFORMATION FOR SEQ ID NO:48:

(i) SEQUENCE CHARACTERISTICS:
(A) LENGTH: 22 amino acids
(B) TYPE: amino acid
(C) STRANDEDNESS:
(D) TOPOLOGY: linear (xi) SEQUENCE DESCRIPTION: SEQ ID NO:48:

```
Cys Ser Asp Cys Ile Val Thr Ala Leu Arg Ser Gly Asn Lys Glu Cys
1               5                   10                  15

Pro Thr Cys Arg Lys Lys
            20
```

(2) INFORMATION FOR SEQ ID NO:49:

(i) SEQUENCE CHARACTERISTICS:
(A) LENGTH: 17 amino acids
(B) TYPE: amino acid
(C) STRANDEDNESS:
(D) TOPOLOGY: linear (xi) SEQUENCE DESCRIPTION: SEQ ID NO:49:

```
Phe Leu Arg Cys Gln Gln Cys Gln Ala Glu Ala Lys Cys Pro Lys Leu
1               5                   10                  15

Leu
```

(2) INFORMATION FOR SEQ ID NO:50:

(i) SEQUENCE CHARACTERISTICS:
(A) LENGTH: 6 amino acids
(B) TYPE: amino acid
(C) STRANDEDNESS:
(D) TOPOLOGY: linear (xi) SEQUENCE DESCRIPTION: SEQ ID NO:50:

```
Pro Cys Leu His Thr Leu
```

-continued 1 5

(2) INFORMATION FOR SEQ ID NO:51:

(i) SEQUENCE CHARACTERISTICS:
(A) LENGTH: 6 amino acids
(B) TYPE: amino acid
(C) STRANDEDNESS:
(D) TOPOLOGY: linear (xi) SEQUENCE DESCRIPTION: SEQ ID NO:51:

Cys Ser Gly Cys Leu Glu
1 5

(2) INFORMATION FOR SEQ ID NO:52:

(i) SEQUENCE CHARACTERISTICS:
(A) LENGTH: 7 amino acids
(B) TYPE: amino acid
(C) STRANDEDNESS:
(D) TOPOLOGY: linear (xi) SEQUENCE DESCRIPTION: SEQ ID NO:52:

Cys Pro Ile Cys Gln Ala Pro
1 5

(2) INFORMATION FOR SEQ ID NO:53:

(i) SEQUENCE CHARACTERISTICS:
(A) LENGTH: 37 base pairs
(B) TYPE: nucleic acid
(C) STRANDEDNESS: single
(D) TOPOLOGY: linear (xi) SEQUENCE DESCRIPTION: SEQ ID NO:53:

ATGGCCCCTG AATGCCCCAG TTTCCGCGGA GGATCTG 37

(2) INFORMATION FOR SEQ ID NO:54:

(i) SEQUENCE CHARACTERISTICS:
(A) LENGTH: 34 base pairs
(B) TYPE: nucleic acid
(C) STRANDEDNESS: single
(D) TOPOLOGY: linear (xi) SEQUENCE DESCRIPTION: SEQ ID NO:54:

CATCACGCCG CAGGCTCTGG CAAAGGCAGG TTTC 34

(2) INFORMATION FOR SEQ ID NO:55:

(i) SEQUENCE CHARACTERISTICS:
(A) LENGTH: 28 base pairs
(B) TYPE: nucleic acid
(C) STRANDEDNESS: single
(D) TOPOLOGY: linear (xi) SEQUENCE DESCRIPTION: SEQ ID NO:55:

AGTAATGACT GTGTAGCACA TGGCACAC 28

(2) INFORMATION FOR SEQ ID NO:56:

(i) SEQUENCE CHARACTERISTICS:
(A) LENGTH: 33 base pairs
(B) TYPE: nucleic acid
(C) STRANDEDNESS: single
(D) TOPOLOGY: linear (xi) SEQUENCE DESCRIPTION: SEQ ID NO:56:

-continued

```
GCGTATAACG CGTTTGGAAT CACTACAGGG ATG                                  33


(2) INFORMATION FOR SEQ ID NO:57:

     (i) SEQUENCE CHARACTERISTICS:
          (A) LENGTH: 33 base pairs
          (B) TYPE: nucleic acid
          (C) STRANDEDNESS: single
          (D) TOPOLOGY: linear

    (xi) SEQUENCE DESCRIPTION: SEQ ID NO:57:

TCAACTGCTT CAGCACATTG TTTTACAAGT GAC                                  33


(2) INFORMATION FOR SEQ ID NO:58:

     (i) SEQUENCE CHARACTERISTICS:
          (A) LENGTH: 33 base pairs
          (B) TYPE: nucleic acid
          (C) STRANDEDNESS: single
          (D) TOPOLOGY: linear

    (xi) SEQUENCE DESCRIPTION: SEQ ID NO:58:

TTTAATACCA CTACAATGGA TGATGTATAT AAC                                  33
```